(12) United States Patent
Moore et al.

US007597723B2

(10) Patent No.: US 7,597,723 B2
(45) Date of Patent: Oct. 6, 2009

(54) UNSUBSTITUTED AND POLYMERIC TRIPHENYMETHANE COLORANTS FOR COLORING CONSUMER PRODUCTS

(75) Inventors: Patrick D Moore, Pacolet, SC (US); Eduardo Torres, Boiling Springs, SC (US)

(73) Assignee: Milliken & Company, Spartanburg, SC (US)

( * ) Notice: Subject to any disclaimer, the term of this patent is extended or adjusted under 35 U.S.C. 154(b) by 77 days.

(21) Appl. No.: 12/012,854

(22) Filed: Feb. 6, 2008

(65) Prior Publication Data

US 2008/0196179 A1 Aug. 21, 2008

Related U.S. Application Data

(60) Provisional application No. 60/900,589, filed on Feb. 9, 2007.

(51) Int. Cl.
*C09B 23/14* (2006.01)
*C09B 11/04* (2006.01)
(52) U.S. Cl. .............................. 8/657; 8/115.54; 8/525; 8/552; 8/659; 552/101
(58) Field of Classification Search ................ 8/657, 8/115.54, 525, 552, 659; 552/101
See application file for complete search history.

(56) References Cited

U.S. PATENT DOCUMENTS

| 2,502,881 | A | 4/1950 | Parker et al. ................. 510/220 |
|---|---|---|---|
| 3,926,830 | A | 12/1975 | Horiguchi et al. ............ 252/135 |
| 4,070,510 | A | 1/1978 | Kahn .......................... 427/385 |
| 4,071,645 | A | 1/1978 | Kahn .......................... 427/340 |
| 4,137,243 | A | 1/1979 | Farmer ........................ 552/255 |
| 5,039,782 | A | 8/1991 | Langer et al. ................ 528/272 |
| 5,567,420 | A | 10/1996 | McEleney et al. ............. 424/60 |
| 5,680,962 | A | 10/1997 | McEleney et al. ......... 222/144.5 |
| 5,753,210 | A | 5/1998 | McEleney et al. ............. 424/59 |
| 5,753,244 | A | 5/1998 | Reynolds et al. ............. 424/401 |
| 5,955,062 | A | 9/1999 | McEleney et al. ............. 424/59 |
| 5,958,383 | A | 9/1999 | McEleney et al. ............. 424/59 |
| 6,042,813 | A | 3/2000 | Fowler ......................... 424/59 |
| 6,086,858 | A | 7/2000 | McEleney et al. ............. 424/59 |
| 6,099,825 | A | 8/2000 | McShane et al. .............. 424/59 |
| 6,331,515 | B1 | 12/2001 | Gambogi et al. ............. 510/424 |
| 6,531,118 | B1 | 3/2003 | Gonzalez et al. .............. 424/59 |
| 6,733,766 | B2 | 5/2004 | Gott et al. ................... 424/401 |
| 6,814,816 | B2 | 11/2004 | Achar et al. ................... 134/26 |
| 6,894,095 | B2 | 5/2005 | Russo et al. ................. 524/249 |
| 7,053,029 | B2 | 5/2006 | MacDonald et al. ......... 510/130 |
| 7,094,812 | B2 * | 8/2006 | Banning et al. .............. 523/160 |
| 7,268,104 | B2 | 9/2007 | Krzysik et al. ............... 510/124 |
| 7,307,051 | B2 | 12/2007 | Rich .......................... 510/138 |
| 2003/0191036 | A1 | 10/2003 | MacDonald et al. ......... 510/141 |
| 2003/0206878 | A1 | 11/2003 | Gott et al. .................... 424/63 |
| 2004/0012622 | A1 | 1/2004 | Russo et al. ................. 345/718 |
| 2004/0014875 | A1 | 1/2004 | Russo et al. ................. 524/557 |
| 2004/0048759 | A1 | 3/2004 | Ribble et al. ................ 510/141 |
| 2004/0065350 | A1 | 4/2004 | Achar et al. ................... 134/18 |
| 2004/0120915 | A1 | 6/2004 | Yang et al. ................ 424/70.13 |
| 2005/0049157 | A1 | 3/2005 | MacDonald et al. ......... 510/130 |
| 2005/0065048 | A1 | 3/2005 | MacDonald et al. ......... 510/141 |
| 2005/0090414 | A1 | 4/2005 | Rich .......................... 510/218 |
| 2005/0288206 | A1 | 6/2005 | Sadlowski et al. ........... 455/442 |
| 2005/0148490 | A1 | 7/2005 | Krzysik et al. ............... 510/490 |
| 2005/0191326 | A1 | 9/2005 | Melker ........................ 424/401 |
| 2005/0192191 | A1 | 9/2005 | Kramer et al. ............... 510/141 |
| 2005/0233918 | A1 | 10/2005 | Rich .......................... 510/136 |
| 2005/0233919 | A1 | 10/2005 | Rich .......................... 510/136 |
| 2006/0008912 | A1 | 1/2006 | Simon ........................... 435/5 |
| 2006/0040835 | A1 | 2/2006 | Newkirk ..................... 510/127 |
| 2006/0051266 | A1 | 3/2006 | Green et al. ................. 422/292 |
| 2006/0058206 | A1 | 3/2006 | Walls et al. .................. 510/130 |
| 2006/0110464 | A1 | 5/2006 | Walls et al. .................. 424/490 |
| 2006/0127425 | A1 | 6/2006 | Walls et al. .................. 424/401 |
| 2006/0144426 | A1 | 7/2006 | Mathews ...................... 134/42 |
| 2006/0222675 | A1 | 10/2006 | Sabnis et al. ................ 424/405 |
| 2006/0236470 | A1 | 10/2006 | Sabnis et al. .................. 8/405 |
| 2006/0257439 | A1 | 11/2006 | Sabnis et al. ................ 424/401 |
| 2006/0287215 | A1 | 12/2006 | McDonald et al. ........... 510/441 |
| 2006/0293205 | A1 | 12/2006 | Chung ........................ 510/383 |
| 2007/0010400 | A1 | 1/2007 | Sabnis et al. ............. 504/116.1 |

(Continued)

OTHER PUBLICATIONS

STIC Search Report dated Jun. 17, 2009.*

(Continued)

*Primary Examiner*—Eisa B Elhilo
(74) *Attorney, Agent, or Firm*—Brenda D. Wentz

(57) ABSTRACT

This invention relates to unsubstituted and polymeric leuco colorants for use as consumer product additives to indicate a product function by color change, to make attractive or distinctive visual effects, or to provide latent or delayed color generation. The colorants may be present in a stable, colorless state and may be transformed to an intense colored state upon exposure to certain physical or chemical changes. Alternatively, the colorants may be transformed from one color to another color upon exposure to certain physical or chemical changes. The colored form of the unsubstituted or polymeric leuco colorant may be transient, since the colorant can revert back to its colorless form or its original color after the physical or chemical activation has been removed or changed. Polymeric leuco colorants are typically comprised of at least two components: at least one leuco chromophore component and at least one polymeric component.

31 Claims, No Drawings

U.S. PATENT DOCUMENTS

| | | |
|---|---|---|
| 2007/0142256 A1 | 6/2007 | Lang et al. .................. 510/141 |
| 2007/0142263 A1 | 6/2007 | Stahl et al. .................. 510/475 |
| 2007/0237807 A1 | 10/2007 | Luu et al. .................. 424/443 |
| 2007/0298085 A1 | 12/2007 | Lestage et al. ............. 424/443 |
| 2008/0196176 A1 | 8/2008 | Torres et al. .................. 8/506 |
| 2008/0196177 A1 | 8/2008 | Moore et al. .................. 8/506 |

OTHER PUBLICATIONS

Chemistry and Applications of Leuco Dyes (edited by Ramaiah Muthyala pp. xi-xiii, 151-152).

* cited by examiner

UNSUBSTITUTED AND POLYMERIC TRIPHENYMETHANE COLORANTS FOR COLORING CONSUMER PRODUCTS

CROSS REFERENCE TO RELATED APPLICATIONS

This application claims priority to U.S. Provisional Patent Application No. 60/900,589, entitled "Unsubstituted and Polymeric Leuco Colorants For Coloring Consumer Products" which was filed on Feb. 9, 2007, and is entirely incorporated by reference herein.

TECHNICAL FIELD

This invention relates to both unsubstituted and polymeric leuco colorants for use as consumer product additives to indicate a product function by color change, to make attractive or distinctive visual effects, or to provide latent or delayed color generation. These types of colorants may be present in a stable, substantially colorless state and may be transformed to an intense colored state upon exposure to certain physical or chemical changes such as, for example, exposure to oxygen, the addition of reducing agents, ion addition, exposure to light, and the like. These types of colorants may also be present in a stable, colored state and may be transformed to a different colored state upon exposure to certain physical or chemical changes. The colored form of the unsubstituted or polymeric leuco colorant may be transient, since the colorant can revert back to its colorless form or original color after the physical or chemical activation has been removed or changed. Some applications would benefit from leuco colorants that generate color and then remain substantially colored. Polymeric leuco colorants are typically comprised of at least two components: at least one leuco chromophore component and at least one polymeric component. These environmentally induced, reversibly-adaptable colorants may be ideal for use in laundry care compositions, household cleaners, ink compositions, waxes, paints, paper, films, foams, thermoplastic materials, coatings and any other product wherein the addition of a colorless polymeric leuco colorant that exhibits color effects only upon exposure to certain environmental catalysts is desired. It is also clear that products can be colored with stable conventional colorants in addition to the leuco colorant, such that a change in shade is observed upon color generation from the leuco colorant.

BACKGROUND

Leuco dyes are known in the prior art to exhibit a change from a colorless or slightly colored state to a state of dark color upon exposure to controlled chemical or physical changes. For example, triphenylmethane ("TPM") compounds, one class of leuco dyes, are useful in applications such as photoimaging and typewritten ribbons whereby microencapsulated TPMs are brought into contact with an acid source and images are generated when pressure or heat is applied. These dyes are described, for example, in *Chemistry and Applications of Leuco Dyes* (edited by Ramaiah Muthyala, pp. xi-xiii; 151-152).

The use of polymeric colorants for coloring consumer products is well known in the prior art. As one non-limiting example, the use of whitening agents, either optical brighteners or blueing agents, in textile applications is known. As textile substrates age, their color tends to fade or yellow due to exposure to light, air, soil, and natural degradation of the fibers that comprise the substrates. Thus, the purpose of whitening agents is generally to visually brighten these textile substrates and counteract the fading and yellowing of the substrates.

Previous attempts to add bluing agents to fabric care products have used preformed pigments or dyes such as azo dyes, triaminotriphenyl methane compounds, triphenyl methane compounds and anthraquinone colorants. U.S. Pat. No. 4,137,243 to Farmer teaches polymeric anthraquinone-derived colorants which exhibit improved light and alkali fastness properties. Farmer also discloses that these colorants may be incorporated into detergent compositions to provide coloration or blueing effect for the detergent composition. These types of colorants must therefore be alkali fast, in order to withstand the alkaline conditions of the detergent composition. The colorants should also be water fugitive so as to not stain the textile articles washed with the colored detergent composition. However, Farmer does not disclose polymeric leuco colorants that have the ability to transform from a colorless to a colored state upon exposure to certain physical or chemical changes.

U.S. Pat. No. 5,039,782 to Langer et al. discloses a copolymer whitening agent that contains a fluorescent group and a hydrophilic group. The whitening agent is preferably 4,4'-bis (carbomethoxystilbene), and the hydrophilic group is preferably a mixture of polyethylene glycol and ethylene glycol. The copolymer optionally contains a hydrophobic monomer portion, such as polyethylene terephthalate, in order to better adhere the polymer to a hydrophobic surface (like polyester fabric or soiled cotton fabric). The resulting copolymer provides dual functionality as a whitening agent and for providing soil release to fabrics. However, it is apparent from the test data provided in Table 3 of the reference that the copolymer fails to provide adequate whitening for soiled cotton fabrics without the addition of a second whitening agent (i.e., Tinopal). Furthermore, Langer et al. fail to disclose polymeric leuco colorants that exhibit a reversible transformation from a colorless to a colored state.

US Patent Application Publication No. 2005/0288206 to Sadlowski et al. discloses the use of hueing dyes in laundry detergent compositions for combating the yellowing of fabrics. The hueing dye is designed to avoid significant build up of the dye on fabric so that the fabric does not exhibit a bluish tint, for example, after repeated exposure to the hueing dye present in laundry detergent. The laundry detergent composition is comprised of a surfactant and a hueing dye. The surfactant may be anionic, nonionic, cationic, zwitterionic, and/or amphoteric in nature. The hueing dye is characterized by having a hueing efficiency of at least 10 and a wash removal value in the range of between 30% and 80%. Exemplary dyes which exhibit these properties include certain categories of dyes that contain blue or violet chromophores, such as triarylmethane dyes, basic dyes, anthraquinone dyes, and azo dyes. However, this reference fails to disclose the use of unsubstituted or polymeric leuco colorants as described by the present invention.

Thus, it is contemplated to be within the scope of the present invention that the polymeric leuco colorants described herein may be ideally suited for use as whitening agents. Many of the whitening agents that are commercially available exhibit a dark color, e.g. a dark blue color, when added to a laundry care composition, such as a laundry detergent, rinse aid, fabric softener, and the like. For instance, the triphenyl methane and thiazolium structures are positively charged colored species. With colored species such as these, the amount of color is visually apparent and may be an undesired shade for consumers. Powdered detergent systems typically use colored speckles to reduce apparent color of the detergent by incorporation of color within the interior of a speckle or granule. Liquid products often incorporate opacity modifiers to reduce the apparent darkness of the product.

The need exists for an effective whitening agent that consumers can use without concern that the garments and other textile substrates will be irreversible stained with the laundry detergent composition that contains a whitening agent. Thus, the colorless polymeric leuco colorants described herein may be added to laundry care compositions without fear of staining, since these colorants are colorless when added to the laundry machine and only exhibit color during the laundry cycle and/or upon exposure to ultraviolet light when the whitening effect is achieved.

The present invention offers advantages over U.S. Pat. Nos. 4,137,243 and 5,039,782 and US Patent Application Publication No. 2005/0288206 as this invention takes advantage of colorless compounds that can be converted to colored compounds with the addition of certain physical and/or chemical catalysts. Such compounds are useful for many consumer products, including, but not limited to, their use as whitening agents in laundry care compositions. As whitening agents, the colored compounds exhibit the desired wavelengths in the range of blue, red, violet, purple, or combinations thereof upon exposure to ultraviolet light (or, they absorb light to produce the same shades) in order to neutralize the yellowness of textile substrates and provide a brightening effect.

SUMMARY

This invention relates to unsubstituted and polymeric leuco colorants and to the method of using such latent colorants in consumer products. Consumer products include, for example laundry care compositions and other household cleaning compositions, as well as any other household textile and non-textile chemical composition. This invention also relates to consumer products that comprise such unsubstituted and polymeric leuco colorants.

DETAILED DESCRIPTION

All patents, published patent applications, and any other publications mentioned in this patent application are herein incorporated entirely by reference.

The present invention relates to several preferred class of leuco dyes which have been discovered to exhibit selective fugitivity, i.e. designed for selective staining or non-staining characteristics in their polymeric form and to also demonstrate the color change transformation when exposed to certain physical or chemical changes. Leuco dyes include the following classes of compounds: spirobenzopyrans, spironaphthooxazines, spirothiopyrans, leuco quinones, leuco anthraquinones, thiazine leuco colorants, oxazine leuco colorants, phenanzine leuco colorants, phthalide based leucos, tetrazolium based leucos, triphenylmethanes, triarylmethanes, fluorans, and leuco diarylmethanes. Potentially preferred classes of leuco compounds may include phthalide triphenylmethane, triaminotriphenyl acetonitriles, and methylene blue colorants. It is contemplated that the unsubstituted and polymeric leuco colorants of the present invention may or may not be encapsulated for use depending on the desired end use of the product containing the colorants.

Triphenylmethane ("TPM") structures of the N,N disubstituted diamino and triaminophenyl methane compounds produce bluish shades that are decolorized by complexation or reaction with strong ions. Examples of suitable ions include, for example, hydroxyl ions, cyanide ions, cyanate ions, and mixtures thereof. The highly alkaline environment needed to produce hydroxyl ions is typically not suitable for products in the neutral to acidic pH range. The cyano product is colorless until exposed to ultraviolet ("UV") light. Upon exposure to UV light, the original blue color is generated and the bluing effect is observed. A laundry care composition may be colored to a consumer pleasing level, and the amount of bluing on the treated textile substrate may be adjusted to the most desirable level. It is also noted that at least some of the colorants of the present invention possess the ability to provide a latent color that is stable to conditions that degrade the colored species. For example, the triphenyl acetoniltrile leuco colorants are stable to strong base and heat while the colored versions degrade. The leuco form of methylene blue is stable to strong reducing agents while most classes of colorants are irreversibly decolorized.

In another embodiment, one approach may be to use colorless blue colorant precursors that are sensitive to oxygen. For example, methylene blue can be reduced to its colorless leuco form. For a practical application, a small amount of reducing agent can be added at the bottling stage to convert the colorant to its colorless form in the closed bottle. Suitable reducing agents include hydrosulfite, reducing sugars, and the like, and mixtures thereof. Thiazolium or other mericyanine dyes may be converted to colorless forms by ion addition.

Finally, blends of conventional optical brighteners or bluing agents and colorless bluing agent precursors can be used to provide whitening effects, whether the effect is achieved immediately upon application or whether it is formulated to provide an increased bluing effect over time or on color generating exposure.

Examples of suitable polymeric constituents that comprise the leuco polymeric colorants include polyoxyalkylene chains having multiple repeating units. Preferably the polymeric constituents include polyoxyalkylene chains having from 2 to about 20 repeating units, and more preferably from 2 to about 10 or even from about 4 to about 6 repeating units. Non-limiting examples of polyoxyalkylene chains include ethylene oxide, propylene oxide, glycidol oxide, butylene oxide and mixtures thereof.

The polymeric leuco colorant of the present invention may be characterized by the following structure:

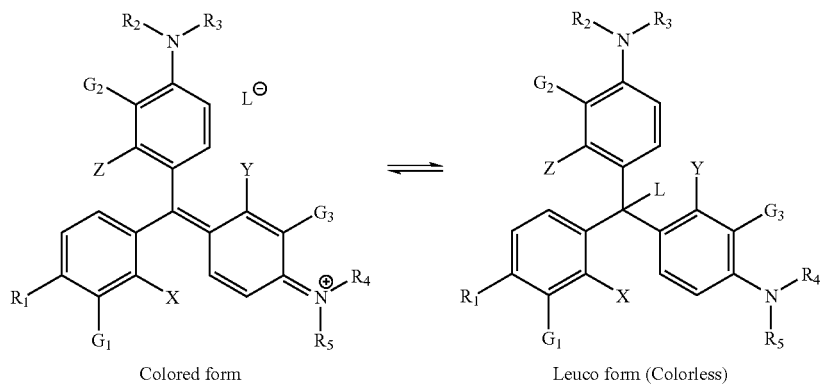

Colored form      Leuco form (Colorless)

wherein:

$R_1$=H, dialkyl amine, diarylamine, alkylamine, hydroxyl, halogen, O-alkyl, or polyalkylene oxide amine;

$R_2$=$C_1$-$C_8$ alkyl, aryl, benzyl, polyalkylene oxide, or glycidylether-polyalkylene oxide wherein the terminal group is selected from hydroxide, $C_1$-$C_{18}$ alkyl ester, and an amino substituted with H, $C_1$-$C_{18}$ alkyl, alkyleneoxide residue, or ammonium quaternary salts derived from alkylation of the amino substituted structure;

$R_3$=$C_1$-$C_8$ alkyl, aryl, benzyl, polyalkylene oxide, or glycidylether-polyalkylene oxide wherein the terminal group is selected from hydroxide, $C_1$-$C_{18}$ alkyl ester, and an amino substituted with H, $C_1$-$C_{18}$ alkyl, alkyleneoxide residue, or ammonium quaternary salts derived from alkylation of the amino substituted structure;

$R_4$=$C_1$-$C_8$ alkyl, aryl, benzyl, polyalkylene oxide, or glycidylether-polyalkylene oxide wherein the terminal group is selected from hydroxide, $C_1$-$C_{18}$ alkyl ester, and an amino substituted with H, $C_1$-$C_{18}$ alkyl, alkyleneoxide residue, or ammonium quaternary salts derived from alkylation of the amino substituted structure;

$R_5$=$C_1$-$C_8$ alkyl, aryl, benzyl, polyalkylene oxide, or glycidylether-polyalkylene oxide wherein the terminal group is selected from hydroxide, $C_1$-$C_{18}$ alkyl ester, and an amino substituted with H, $C_1$-$C_{18}$ alkyl, alkyleneoxide residue, or ammonium quaternary salts derived from alkylation of the amino substituted structure;

wherein X=alkyl, H, sulfonate, or carboxylate; $G_{1-3}$, Y, and Z are independently selected from the group of alkyl, H, halogen, nitro, and O-alkyl;

wherein L=$C_1$-$C_{16}$ alkoxide, phenoxide, bisphenoxide, nitrite, nitrile, alkyl amine, imidazole, arylamine, polyalkylene oxide, alkylsulfide, aryl sulfide, or phosphine oxide;

wherein X and $G_1$ taken together may form an aromatic or heteroaromatic ring;

wherein Y and $G_3$ taken together may form an aromatic or heteroaromatic ring;

wherein Z and $G_2$ taken together may form an aromatic or heteroaromatic ring;

wherein $R_2$ and $G_2$ taken together may form an aromatic or heteroaromatic ring;

wherein $R_4$ and $G_3$ taken together may form an aromatic or heteroaromatic ring.

The polymeric leuco colorant of the present invention may also be characterized by the following structure:

wherein:

$R_1$=H, alkyl, aryl, or alkyl-aryl wherein the terminal group is selected from hydroxide, $C_1$-$C_{18}$ alkyl ester, and an amino substituted with H, $C_1$-$C_{18}$ alkyl, alkyleneoxide residue, or ammonium quaternary salts derived from alkylation of the amino substituted structure;

$R_2$=H, alkyl, aryl, or alkyl-aryl wherein the terminal group is selected from hydroxide, $C_1$-$C_{18}$ alkyl ester, and an amino substituted with H, $C_1$-$C_{18}$ alkyl, alkyleneoxide residue, or ammonium quaternary salts derived from alkylation of the amino substituted structure;

$R_3$=H, polyalkylene oxide, or glycidylether-polyalkylene oxide wherein the terminal group is selected from hydroxide, $C_1$-$C_{18}$ alkyl ester, and an amino substituted with H, $C_1$-$C_{18}$ alkyl, alkyleneoxide residue, or ammonium quaternary salts derived from alkylation of the amino substituted structure;

$R_4$=$C_1$-$C_{18}$ alkyl, aryl, benzyl, polyalkylene oxide, or glycidylether-polyalkylene oxide wherein the terminal group is selected from hydroxide, $C_1$-$C_{18}$ alkyl ester, and an amino substituted with H, $C_1$-$C_{18}$ alkyl, alkyleneoxide residue, or ammonium quaternary salts derived from alkylation of the amino substituted structure; and $R_5$=H, alkyl, or halogen; and $R_6$=H, alkyl, or halogen.

In one aspect, suitable polymeric leuco colorants are set forth in Table 1 below. The corresponding chemical names, as determined by ChemFinder software Level:Pro; Version 9.0 available from CambridgeSoft, Cambridge, Mass., U.S.A., for such colorants are respectively provided in Table 2 below.

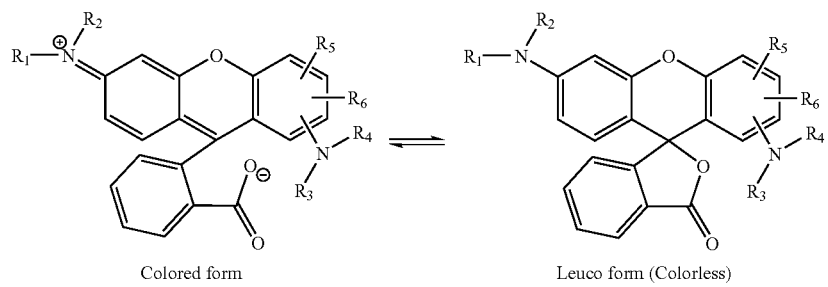

Colored form      Leuco form (Colorless)

TABLE 1
Structures for Polymeric Leuco Colorants
(includes fluorans and lactone-TPM)
| Colorant | Structure |
|---|---|
| 1 | 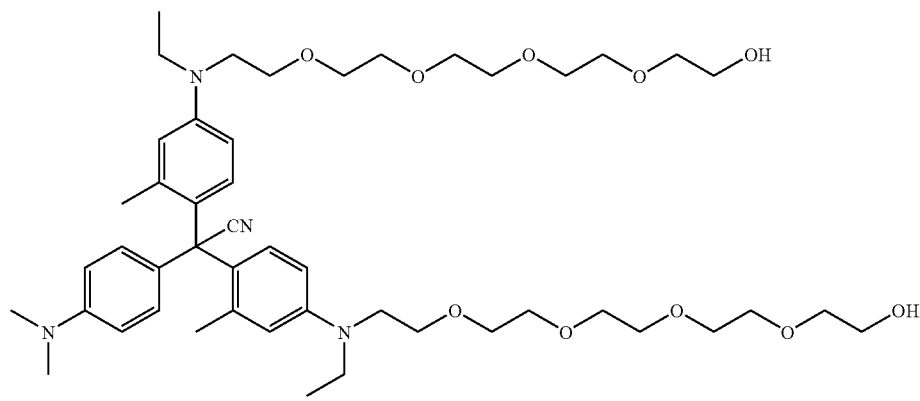 |
| 2 | 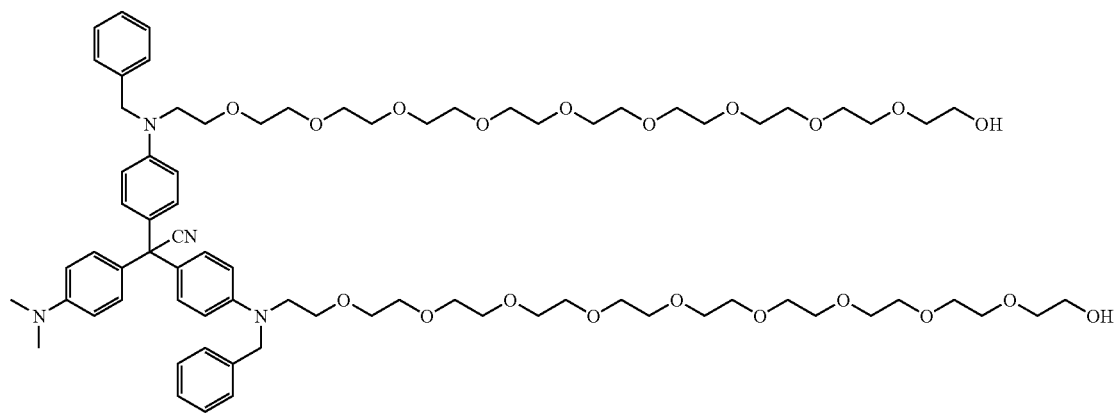 |
| 3 | 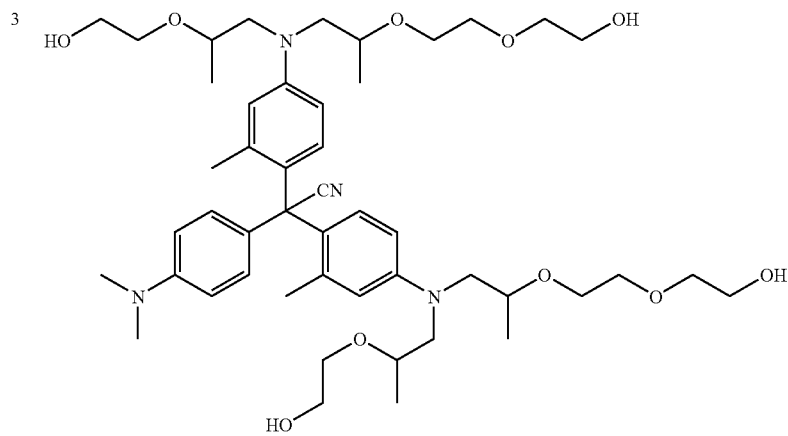 |

TABLE 1-continued
Structures for Polymeric Leuco Colorants
(includes fluorans and lactone-TPM)
Colorant | Structure
4
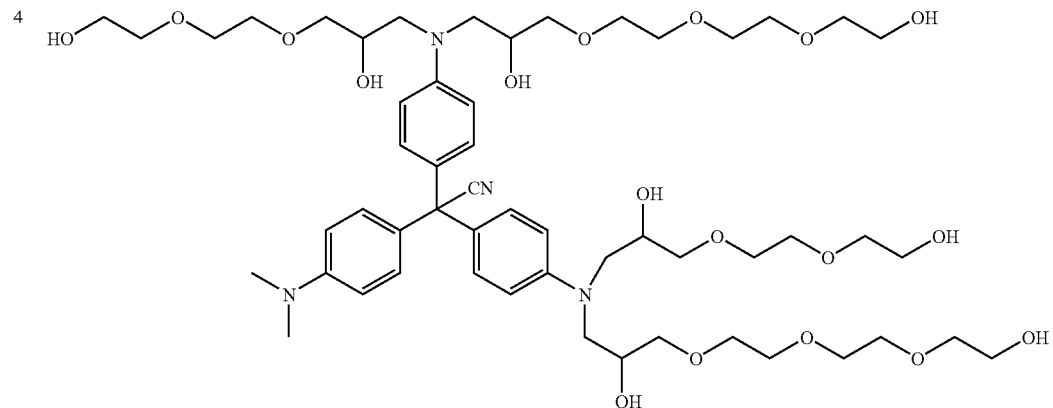
5
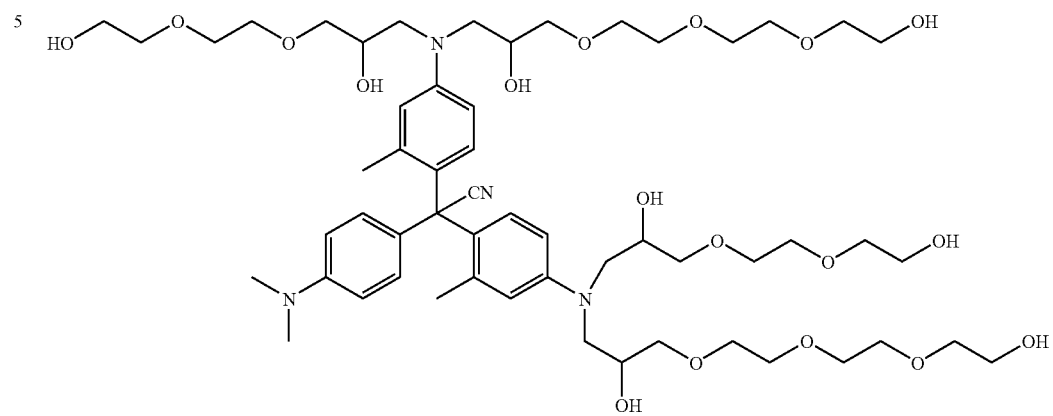
6
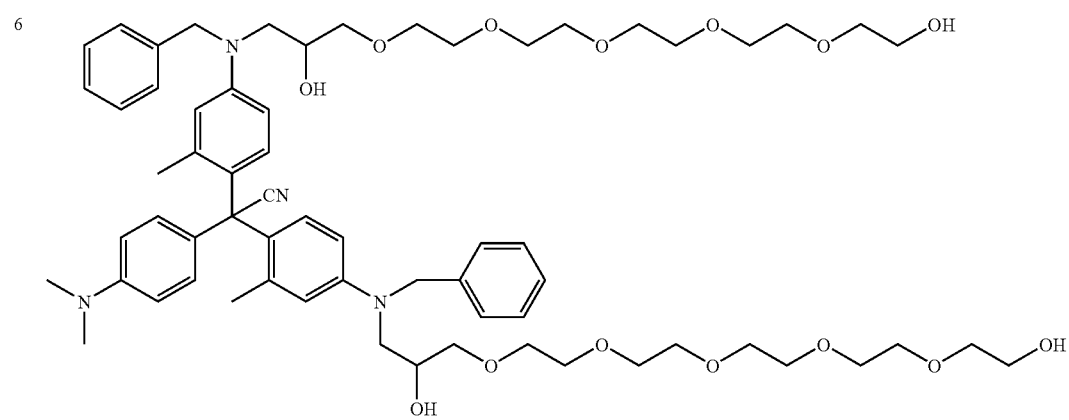

TABLE 1-continued
Structures for Polymeric Leuco Colorants
(includes fluorans and lactone-TPM)
| Colorant | Structure |
|---|---|
| 7 | 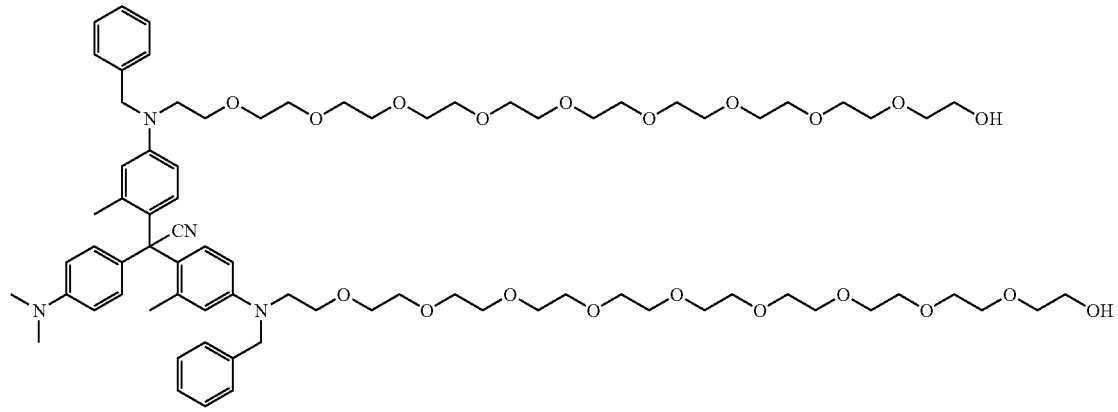 |
| 8 | 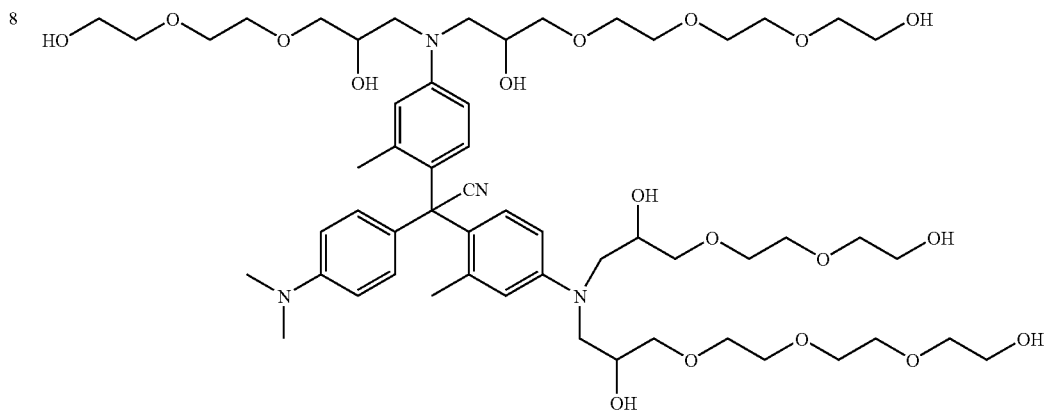 |
| 9 | 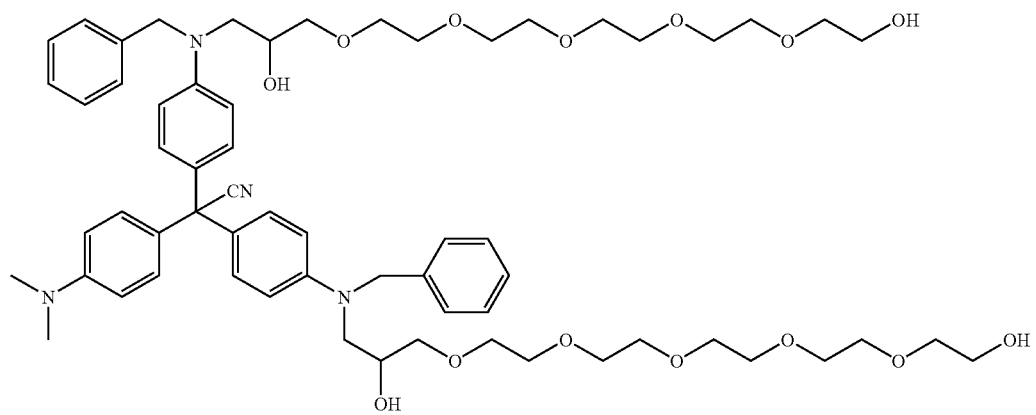 |

TABLE 1-continued
Structures for Polymeric Leuco Colorants
(includes fluorans and lactone-TPM)
Colorant | Structure
10 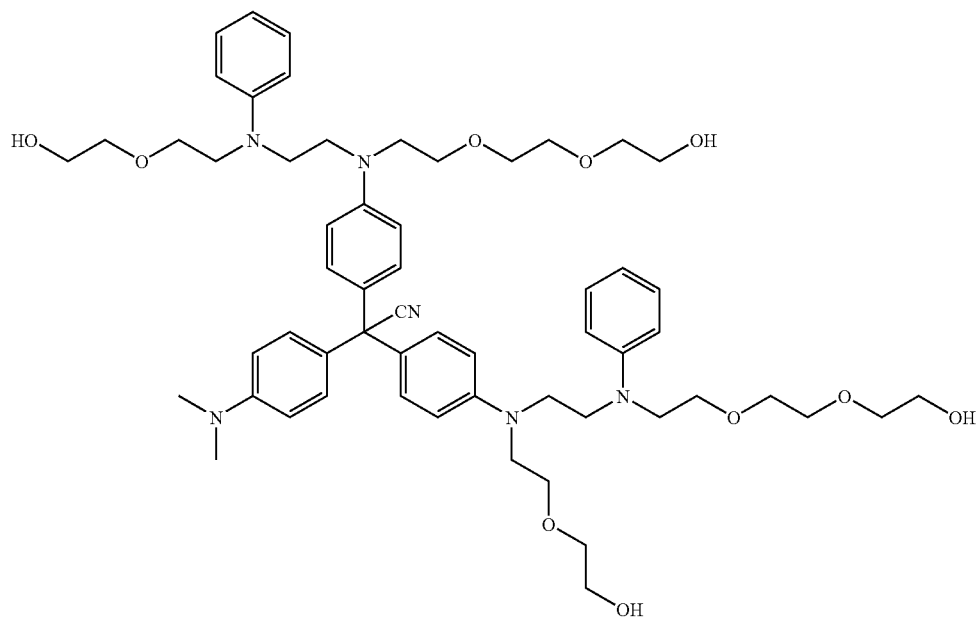
11 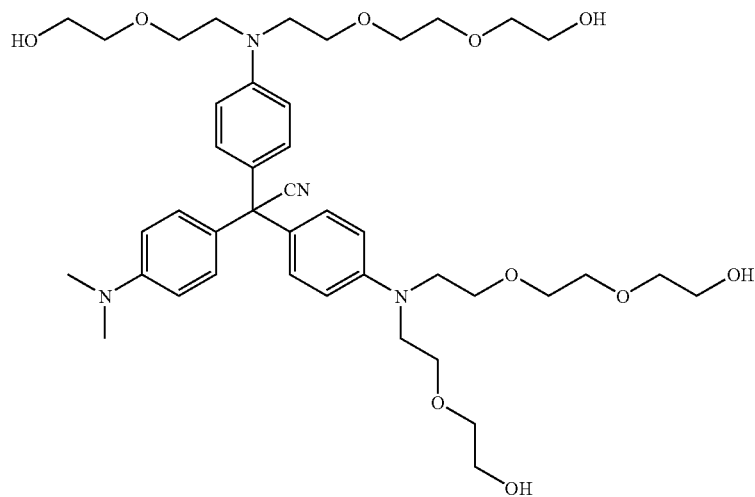

TABLE 1-continued
Structures for Polymeric Leuco Colorants
(includes fluorans and lactone-TPM)
Colorant Structure
12 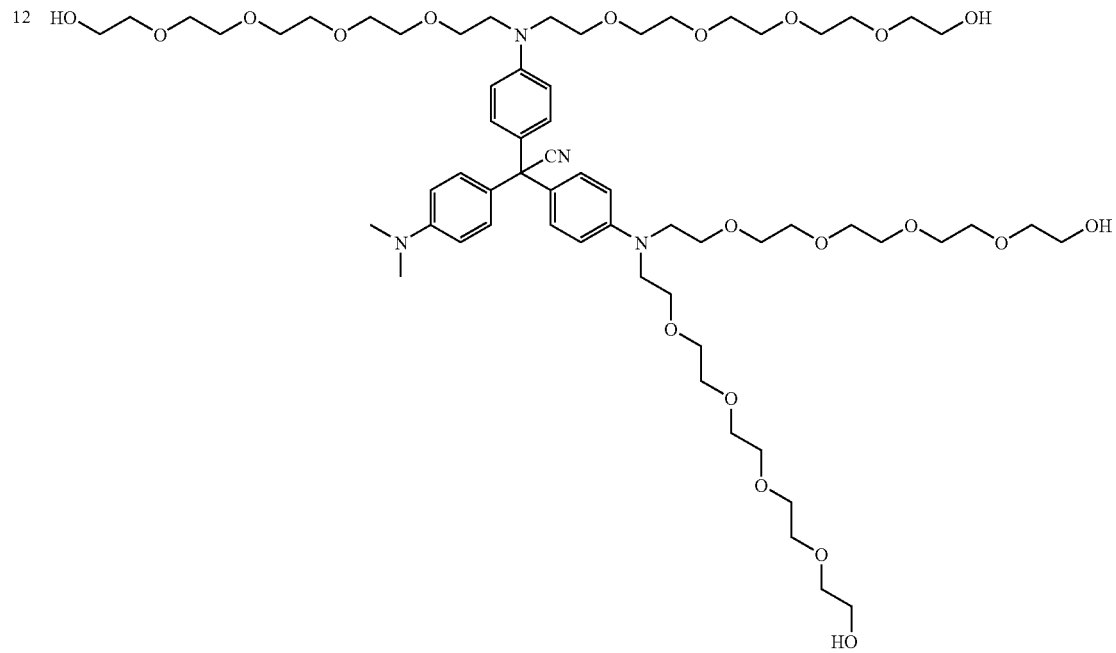
13 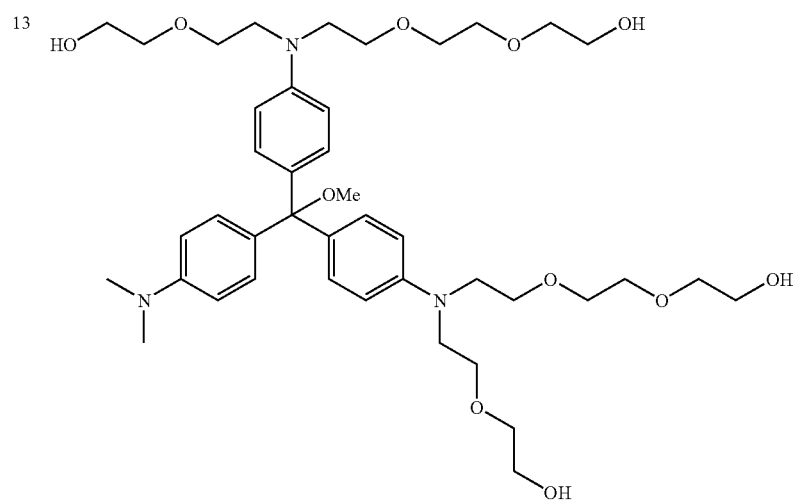

TABLE 1-continued
Structures for Polymeric Leuco Colorants
(includes fluorans and lactone-TPM)
Colorant Structure
14
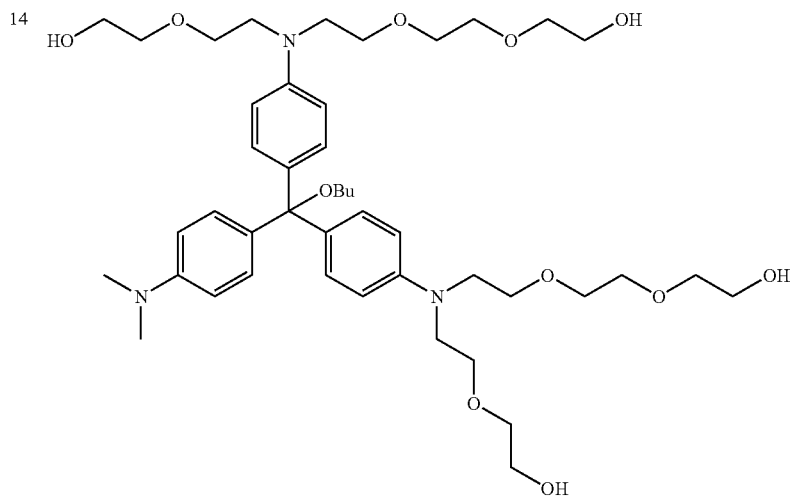
15
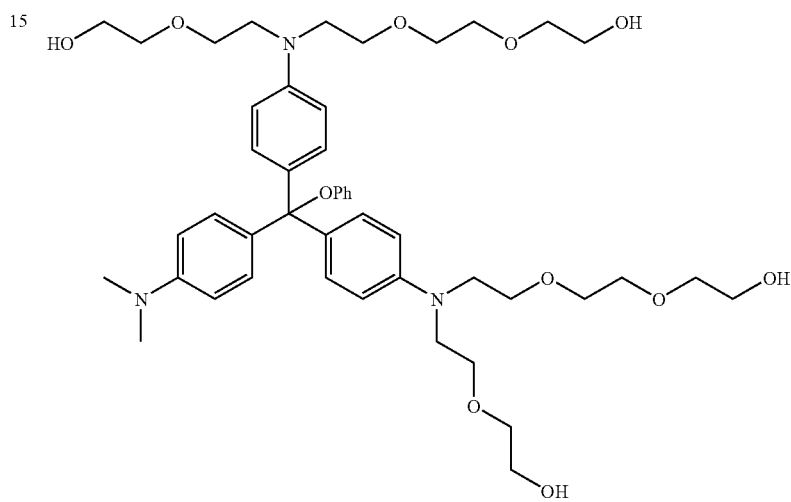
16
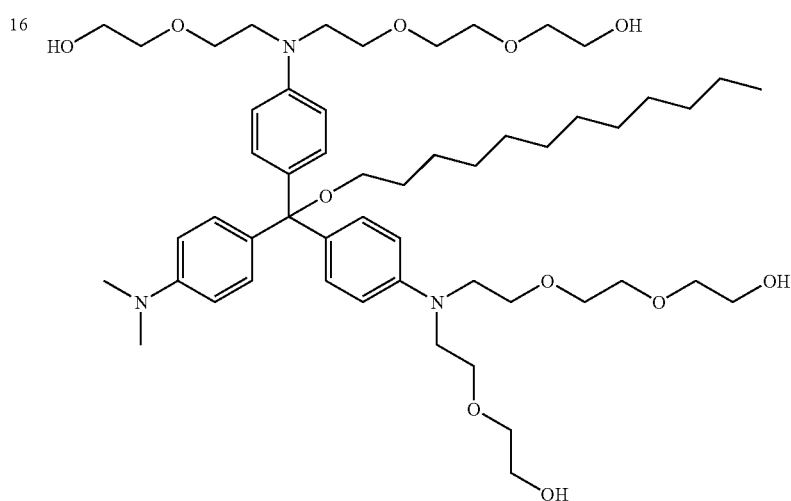

TABLE 1-continued
Structures for Polymeric Leuco Colorants
(includes fluorans and lactone-TPM)
Colorant Structure
17
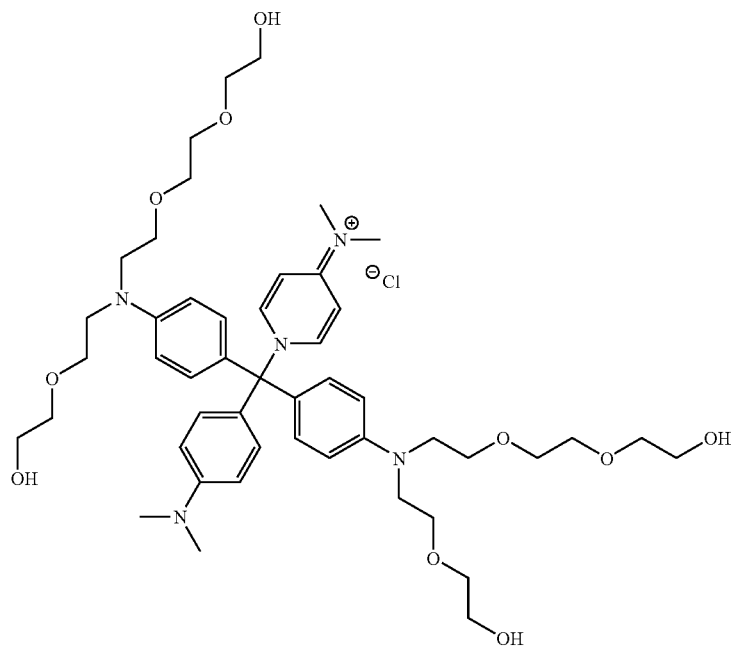
18
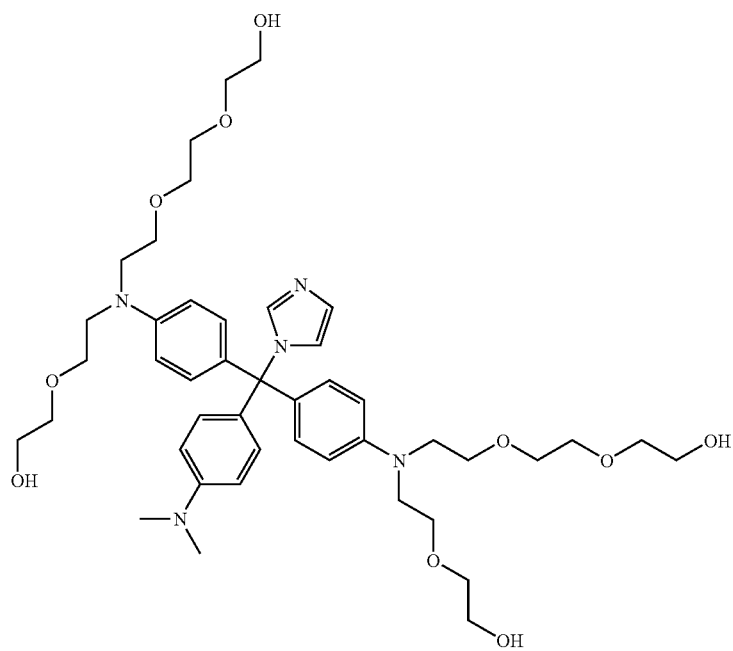

TABLE 1-continued
Structures for Polymeric Leuco Colorants
(includes fluorans and lactone-TPM)
Colorant | Structure
19 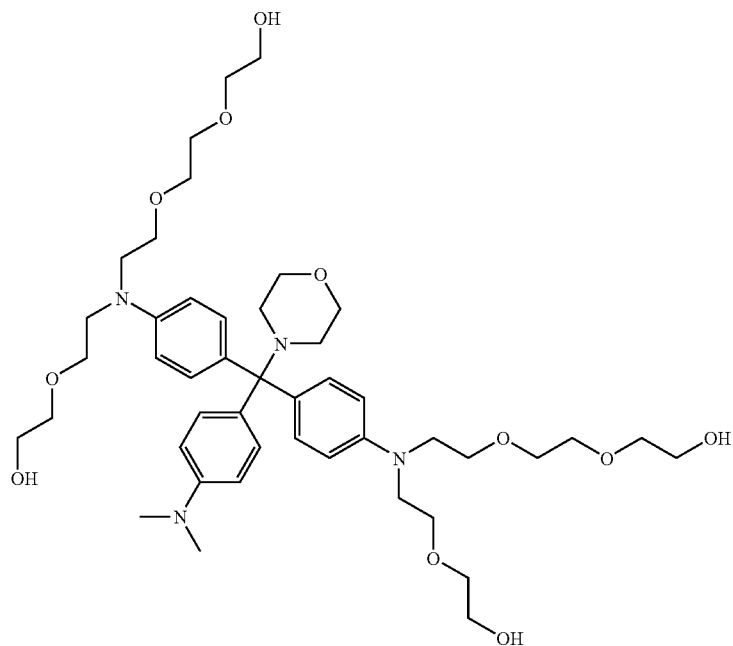
20 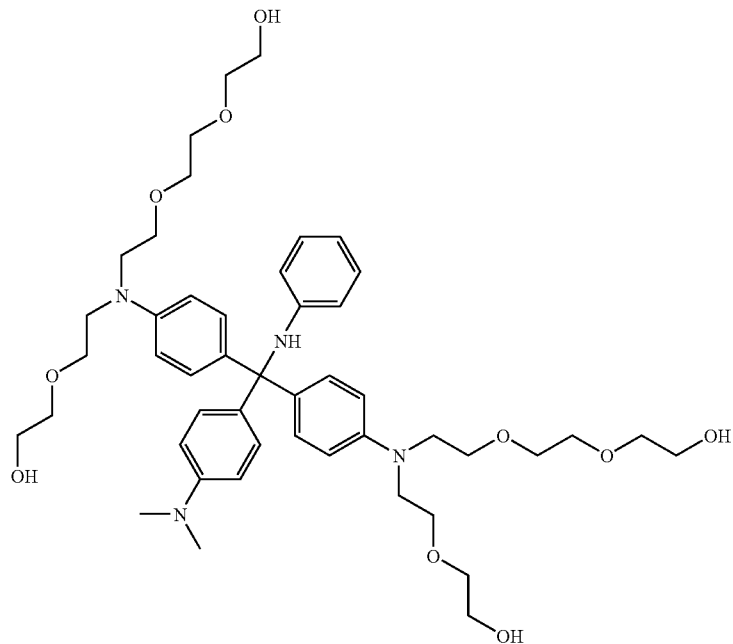

TABLE 1-continued
Structures for Polymeric Leuco Colorants
(includes fluorans and lactone-TPM)
| Colorant | Structure |
|---|---|
| 21 | 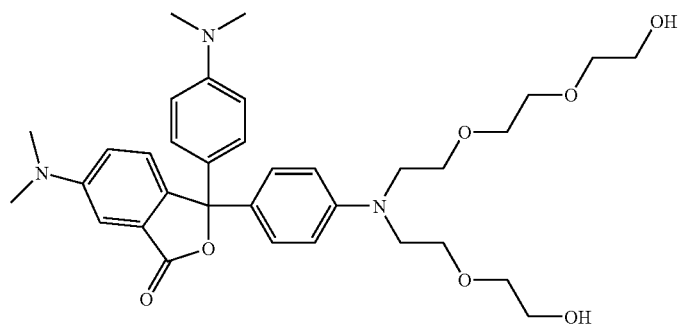 |
| 22 | 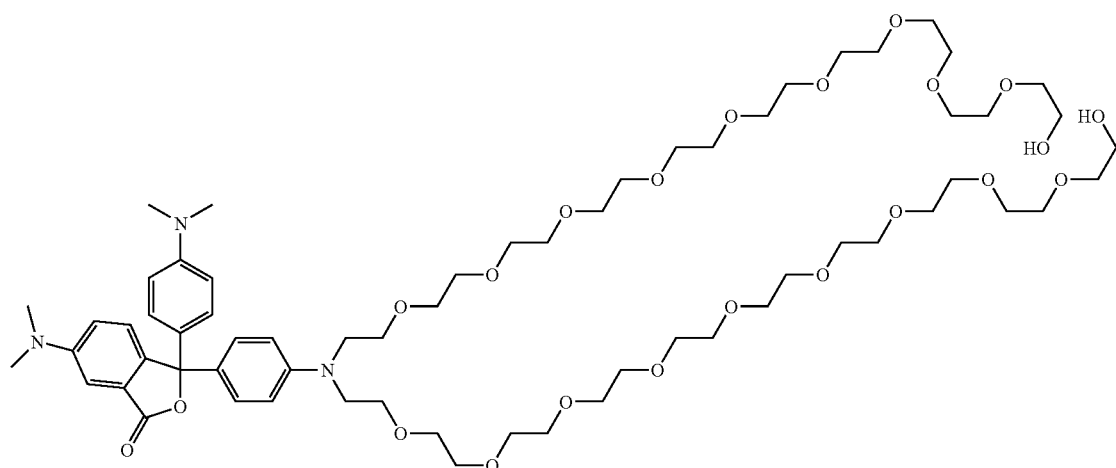 |
| 23 | 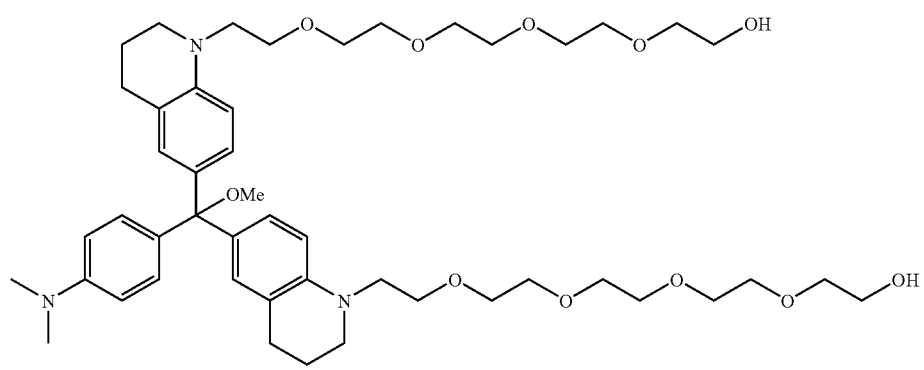 |
| 24 | 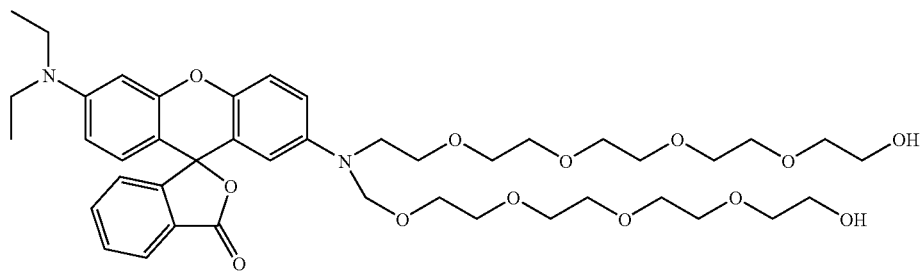 |

TABLE 1-continued

Structures for Polymeric Leuco Colorants
(includes fluorans and lactone-TPM)

| Colorant | Structure |
|---|---|
| 25 | *(structure: triphenylmethane leuco dye with OMe and o-SO$_3^-$Na$^+$ group; two para-amino groups bearing tetraethyleneglycol chains terminating in OH)* |
| 26 | *(structure: triphenylmethane leuco dye with CN group; two para-amino groups bearing tetraethyleneglycol chains terminating in OH)* |

TABLE 1-continued
Structures for Polymeric Leuco Colorants
(includes fluorans and lactone-TPM)
Colorant Structure
27
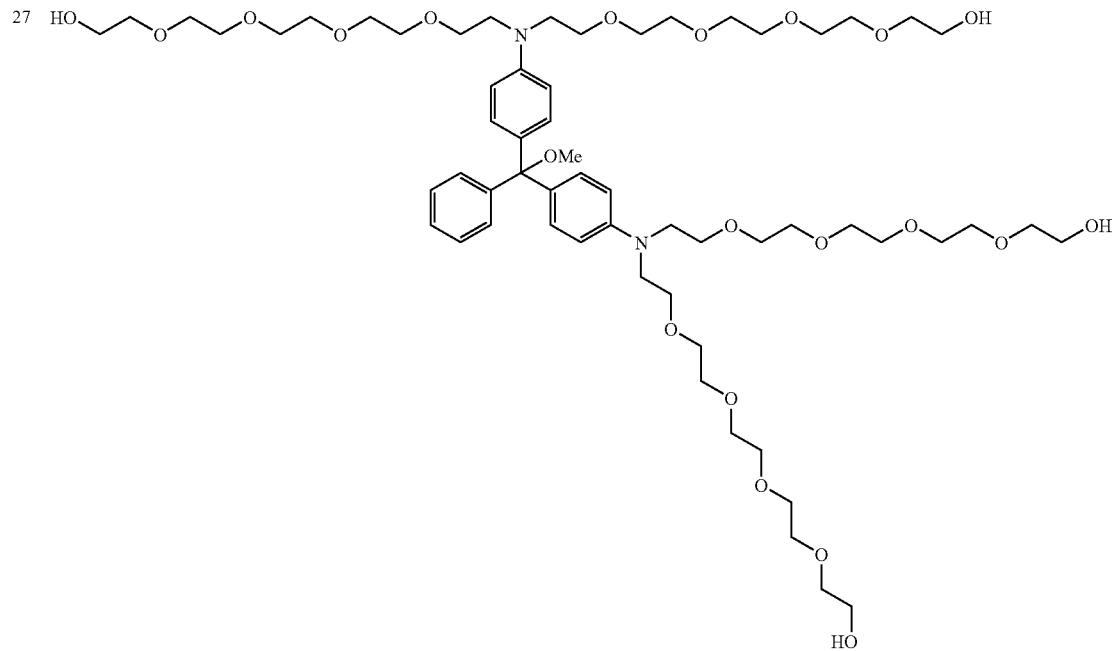
28
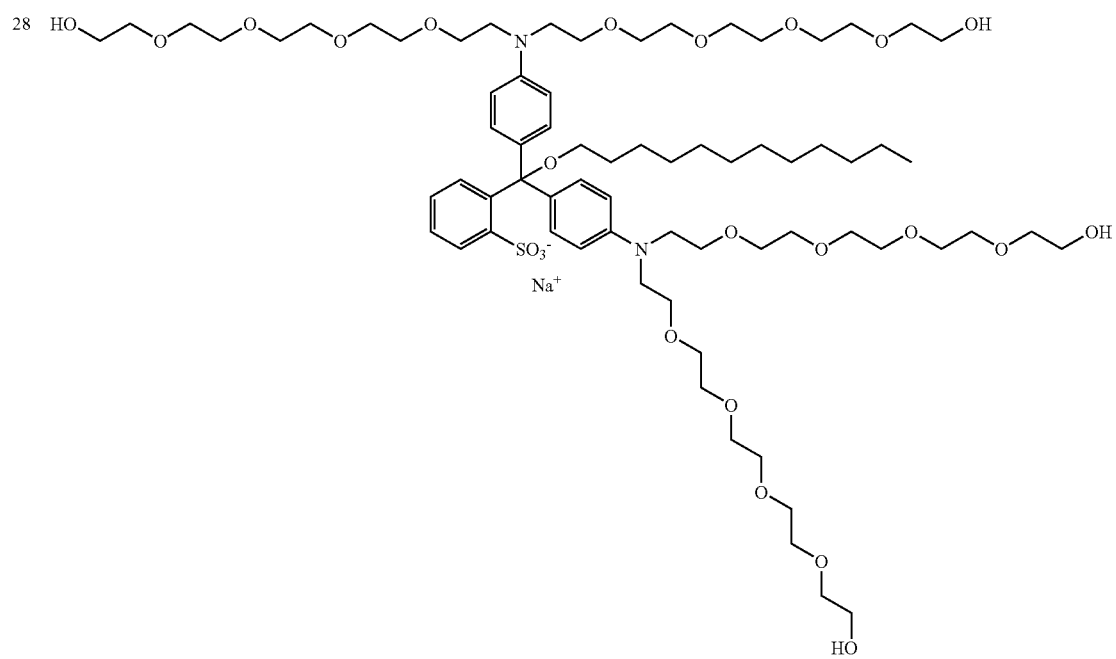

TABLE 2

Chemical Names for Structures Provided in Table 1

| Colorant | IUPAC Name |
|---|---|
| 1 | (4-Dimethylamino-phenyl)-bis-(4-{ethyl-[2-(2-{2-[2-(2-hydroxy-ethoxy)-ethoxy]-ethoxy}-ethoxy)-ethyl]-amino}-2-methyl-phenyl)-acetonitrile |
| 2 | Bis-{4-[benzyl-(2-{2-[2-(2-{2-[2-(2-{2-[2-(2-hydroxy-ethoxy)-ethoxy]-ethoxy}-ethoxy)-ethoxy]-ethoxy}-ethoxy)-ethoxy]-ethoxy}-ethyl)-amino]-phenyl}-(4-dimethylamino-phenyl)-acetonitrile |
| 3 | (4-Dimethylamino-phenyl)-bis-(4-{{2-[2-(2-hydroxy-ethoxy)-ethoxy]-propyl}-[2-(2-hydroxy-ethoxy)-propyl]-amino}-2-methyl-phenyl)-acetonitrile |
| 4 | (4-Dimethylamino-phenyl)-bis-[4-((2-hydroxy-3-{2-[2-(2-hydroxy-ethoxy)-ethoxy]-ethoxy}-propyl)-{2-hydroxy-3-[2-(2-hydroxy-ethoxy)-ethoxy]-propyl}-amino)-phenyl]-acetonitrile |
| 5 | (4-Dimethylamino-phenyl)-bis-[4-((2-hydroxy-3-{2-[2-(2-hydroxy-ethoxy)-ethoxy]-ethoxy}-propyl)-{2-hydroxy-3-[2-(2-hydroxy-ethoxy)-ethoxy]-propyl}-amino)-2-methyl-phenyl]-acetonitrile |
| 6 | Bis-[4-(benzyl-{2-hydroxy-3-[2-(2-{2-[2-(2-hydroxy-ethoxy)-ethoxy]-ethoxy}-ethoxy)-ethoxy]-propyl}-amino)-2-methyl-phenyl]-(4-dimethylamino-phenyl)-acetonitrile |
| 7 | Bis-{4-[benzyl-(2-{2-[2-(2-{2-[2-(2-{2-[2-(2-hydroxy-ethoxy)-ethoxy]-ethoxy}-ethoxy)-ethoxy]-ethoxy}-ethoxy)-ethoxy]-ethoxy}-ethyl)-amino]-2-methyl-phenyl}-(4-dimethylamino-phenyl)-acetonitrile |
| 8 | (4-Dimethylamino-phenyl)-bis-[4-((2-hydroxy-3-{2-[2-(2-hydroxy-ethoxy)-ethoxy]-ethoxy}-propyl)-{2-hydroxy-3-[2-(2-hydroxy-ethoxy)-ethoxy]-propyl}-amino)-2-methyl-phenyl]-acetonitrile |
| 9 | Bis-[4-(benzyl-{2-hydroxy-3-[2-(2-{2-[2-(2-hydroxy-ethoxy)-ethoxy]-ethoxy}-ethoxy)-ethoxy]-propyl}-amino)-phenyl]-(4-dimethylamino-phenyl)-acetonitrile |
| 10 | (4-Dimethylamino-phenyl)-{4-[{2-[2-(2-hydroxy-ethoxy)-ethoxy]-ethyl}-(2-{[2-(2-hydroxy-ethoxy)-ethyl]-phenyl-amino}-ethyl)-amino]-phenyl}-{4-[[2-(2-hydroxy-ethoxy)-ethoxy-ethyl]-(2-{[2-(2-hydroxy-ethoxy)-ethyl]-phenyl-amino}-ethyl)-amino]-phenyl}-acetonitrile |
| 11 | (4-Dimethylamino-phenyl)-bis-(4-{{2-[2-(2-hydroxy-ethoxy)-ethoxy]-ethyl}-[2-(2-hydroxy-ethoxy)-ethyl]-amino}-phenyl)-acetonitrile |
| 12 | Bis-(4-{bis-[2-(2-{2-[2-(2-hydroxy-ethoxy)-ethoxy]-ethoxy}-ethoxy)-ethyl]-amino}-phenyl)-(4-dimethylamino-phenyl)-acetonitrile |
| 13 | 2-[2-(2-{{4-[(4-Dimethylamino-phenyl)-(4-{{2-[2-(2-hydroxy-ethoxy)-ethoxy]-ethyl}-[2-(2-hydroxy-ethoxy)-ethyl]-amino}-phenyl)-methoxy-methyl]-phenyl}-[2-(2-hydroxy-ethoxy)-ethyl]-amino}-ethoxy)-ethoxy]-ethanol |
| 14 | 2-[2-(2-{{4-[Butoxy-(4-dimethylamino-phenyl)-(4-{{2-[2-(2-hydroxy-ethoxy)-ethoxy]-ethyl}-[2-(2-hydroxy-ethoxy)-ethyl]-amino}-phenyl)-methyl]-phenyl}-[2-(2-hydroxy-ethoxy)-ethyl]-amino}-ethoxy)-ethoxy]-ethanol |
| 15 | 2-[2-(2-{{4-[(4-Dimethylamino-phenyl)-(4-{{2-[2-(2-hydroxy-ethoxy)-ethoxy]-ethyl}-[2-(2-hydroxy-ethoxy)-ethyl]-amino}-phenyl)-phenoxy-methyl]-phenyl}-[2-(2-hydroxy-ethoxy)-ethyl]-amino}-ethoxy)-ethoxy]-ethanol |
| 16 | 2-[2-(2-{{4-[(4-Dimethylamino-phenyl)-dodecyloxy-(4-{{2-[2-(2-hydroxy-ethoxy)-ethoxy]-ethyl}-[2-(2-hydroxy-ethoxy)-ethyl]-amino}-phenyl)-methyl]-phenyl}-[2-(2-hydroxy-ethoxy)-ethyl]-amino}-ethoxy)-ethoxy]-ethanol |
| 17 | {1-[(4-Dimethylamino-phenyl)-bis-(4-{{2-[2-(2-hydroxy-ethoxy)-ethoxy]-ethyl}-[2-(2-hydroxy-ethoxy)-ethyl]-amino}-phenyl)-methyl]-1H-pyridin-4-ylidene}-dimethyl-ammonium; chloride |
| 18 | 2-[2-(2-{{4-[(4-Dimethylamino-phenyl)-(4-{{2-[2-(2-hydroxy-ethoxy)-ethoxy]-ethyl}-[2-(2-hydroxy-ethoxy)-ethyl]-amino}-phenyl)-imidazol-1-yl-methyl]-phenyl}-[2-(2-hydroxy-ethoxy)-ethyl]-amino}-ethoxy)-ethoxy]-ethanol |
| 19 | 2-[2-(2-{{4-[(4-Dimethylamino-phenyl)-(4-{{2-[2-(2-hydroxy-ethoxy)-ethoxy]-ethyl}-[2-(2-hydroxy-ethoxy)-ethyl]-amino}-phenyl)-morpholin-4-yl-methyl]-phenyl}-[2-(2-hydroxy-ethoxy)-ethyl]-amino}-ethoxy)-ethoxy]-ethanol |
| 20 | 2-[2-(2-{{4-[(4-Dimethylamino-phenyl)-(4-{{2-[2-(2-hydroxy-ethoxy)-ethoxy]-ethyl}-[2-(2-hydroxy-ethoxy)-ethyl]-amino}-phenyl)-phenylamino-methyl]-phenyl}-[2-(2-hydroxy-ethoxy)-ethyl]-amino}-ethoxy)-ethoxy]-ethanol |
| 21 | 6-Dimethylamino-3-(4-dimethylamino-phenyl)-3-(4-{{2-[2-(2-hydroxy-ethoxy)-ethoxy]-ethyl}-[2-(2-hydroxy-ethoxy)-ethyl]-amino}-phenyl)-3H-isobenzofuran-1-one |
| 22 | 3-{4-[Bis-(2-{2-[2-(2-{2-[2-(2-{2-[2-(2-hydroxy-ethoxy)-ethoxy]-ethoxy}-ethoxy)-ethoxy]-ethoxy}-ethoxy)-ethoxy]-ethoxy}-ethyl)-amino]-phenyl}-6-dimethylamino-3-(4-dimethylamino-phenyl)-3H-isobenzofuran-1-one |
| 23 | 2-{2-[2-(2-{2-[6-((4-Dimethylamino-phenyl)-{1-[2-(2-{2-[2-(2-hydroxy-ethoxy)-ethoxy]-ethoxy}-ethoxy)-ethyl]-1,2,3,4-tetrahydro-quinolin-6-yl}-methoxy-methyl)-3,4-dihydro-2H-quinolin-1-yl]-ethoxy}-ethoxy)-ethoxy]-ethoxy}-ethanol |
| 24 | 2-{6-Diethylamino-2-[[2-(2-{2-[2-(2-hydroxy-ethoxy)-ethoxy]-ethoxy}-ethoxy)-ethyl]-(2-{2-[2-(2-hydroxy-ethoxy)-ethoxy]-ethoxy}-ethoxymethyl)-amino]-9H-xanthen-9-yl}-fluoran |
| 25 | Sodium; 2-[bis-(4-{bis-[2-(2-{2-[2-(2-hydroxy-ethoxy)-ethoxy]-ethoxy}-ethoxy)-ethyl]-amino}-phenyl)-methoxy-methyl]-benzenesulfonate |
| 26 | Bis-(4-{bis-[2-(2-{2-[2-(2-hydroxy-ethoxy)-ethoxy]-ethoxy}-ethoxy)-ethyl]-amino}-phenyl)-phenyl-acetonitrile |
| 27 | 2-(2-{2-[2-(2-{{4-[(4-{Bis-[2-(2-{2-[2-(2-hydroxy-ethoxy)-ethoxy]-ethoxy}-ethoxy)-ethyl]-amino}-phenyl)-methoxy-phenyl-methyl]-phenyl}-[2-(2-{2-[2-(2-hydroxy-ethoxy)-ethoxy]-ethoxy}-ethoxy)-ethyl]-amino}-ethoxy)-ethoxy]-ethoxy}-ethoxy)-ethanol |
| 28 | Sodium; 2-[bis-(4-{bis-[2-(2-{2-[2-(2-hydroxy-ethoxy)-ethoxy]-ethoxy}-ethoxy)-ethyl]-amino}-phenyl)-dodecyloxy-methyl]-benzenesulfonate |

The Colorants provided in Tables 1 and 2 vary in the way they are transformed from their colorless to colored state. For example, Colorants 1-12 can generate color upon exposure to UV light. Colorants 13, 16, 17, 19 and 28 can generate color upon exposure to heat. Colorants 13-16, 18, 21 and 24 generate color upon salvation or ion addition (halochromics). Colorants 21, 22, and 24 generate color on exposure to acid. The methylene blue leuco dye family generates color on exposure to air.

There are a wide variety of possible applications of polymeric leuco colorants. Possible uses of these colorants include, for example, spray pattern indicators that are applied in a colorless state and then develop color upon exposure to UV light or oxygen. Alternatively, the inverse situation may be conceivable wherein a spray pattern indicator is applied to a substrate in a colored state and its color disappears after exposure to a chemical or physical catalyst, such as UV light or oxygen.

Other uses of the polymeric leuco colorants of the present invention include their incorporation as additives for color change in consumer products such as, for example, products packaged in opaque containers that, when initially dispensed, are colorless but develop color upon exposure to air or light or water. This application may be useful in showing activation or evenness of application. Another embodiment may include an initially conventionally colored liquid product that changes color after being dispensed from a container. For instance, the product may change from yellow to green by the addition of a blue shade of the colorant. A variation of this concept may include the shade matched color that becomes color balanced to a grey shade after the leuco color develops. This has the visual effect of turning from colored to colorless, since grey shades are much more difficult to observe.

Another example of color change additives in consumer products includes products packaged in visually transparent containers that are made of plastics or formulated plastics that block UV light. After dispensing from the container, a color may be formed by exposure to ambient UV light. Yet another embodiment includes products that are packaged in UV transparent containers where the shade of the product depends on direction and intensity of light—the color intensity being greatest near the wall of the container and decreasing into the interior of the container. The distance of color formation may be dependent upon light intensity, rate of color migration, and formulation of other light absorbers contained therein.

Other uses of polymeric leuco colorants may include transparent containers (e.g. thermoplastic containers) with negative image printed with UV absorbing but visually transparent image. The color change in this embodiment may occur in the UV exposed surface liquid to provide an image or logo that is present in the liquid product. Other uses include incorporation of polymeric leuco colorants into molded plastic parts and/or containers that also contain high levels of UV blocker so that that the plastic part or container can only change color under very high intensity light. This application may also provide containers that have logos or other design features that are difficult to produce by conventional means. It may also allow for covered sections on sealed containers that reveal tampering when exposed to UV light.

Further examples of the use of the polymeric leuco colorants include incorporation into consumer products such as toilet bowl products that are protected from light in the water tank but then turn color upon exposure to UV light when dispensed into the toilet bowl; colored emulsions that allow only surface penetration of light giving a two color effect; solid consumer products like soap bars, bath powders, and laundry powders wherein the surface is colored but the interior contains the original color; and tamper evident seals and messages printed with inks containing colorless polymeric leuco colorants that, when exposed to light or air, transform to their colored state.

It is also contemplated that the polymeric leuco colorants may be incorporated into children's creative art products such as, for example, finger paints that change color during use; colorless paper that generates color when painted with water or pH adjusting fluids; shadow box image formation prepared by placing objects on paper or film coated with polymeric leuco colorants and then exposing the substrate to UV light; preventing additional color formation on a substrate by a suitable mechanism like covering the substrate with a UV absorbing film or coating; crayons or soft pencils that write one color and then develop a second color upon exposure to UV light; colored liquid markers and pens that dispense one shade and then change color; and molding clay products that change surface color upon exposure to oxygen or UV light.

Other embodiments include incorporation of polymeric leuco colorants into cosmetic formulations and compositions for the purpose of providing a lightening or "glowing" effect upon exposure to oxygen or UV light. This includes coloration effects for hair wherein color change occurs upon outdoor exposure or the removal of intense light. The colorants may also be used for tinting films for housing and automobile windows that have the effect of lightening in a low light environment. The colorants may also be used as expiration date indicators, temperature indicators (e.g. meat cooking temperature indicators), and fuel indicators for measuring the presence of water.

Other possible applications for the unsubstituted and polymeric leuco colorants described herein include: pattern indicator for cleaning compositions (such as coverage indicators for mopping, cleaning, car polishing, etc.); image development over time with UV exposure (such as a picture image that changes over time); light bulbs that change color as they get hotter; wires that change color as they get hot or wet as a safety indicator; colorants combined with encapsulated triggers (such as a color that changes upon exposure to water etc. mixed with encapsulated water) that when pressure is applied provides color change (the colorant can also be encapsulated); UV light and moisture triggers could be used for any number of lifetime timers; urine indicator for children's sheets and/or mattresses (possibly a washable feature); and deodorant that releases bluing agent on exposure to sweat (valeric acid, etc.) to reverse the yellowing of white shirts in the arm pits.

The polymeric leuco colorants described in the present specification may be incorporated for use as whitening agents into a laundry care composition. Laundry care compositions include, but are not limited to, laundry detergents and fabric care compositions such as, for example, liquid and/or powder laundry detergent formulations and rinse added fabric softening (RAFS) compositions. Such compositions comprise one or more of said whitening agents and a laundry care ingredient. The whitening agent may be present in the laundry care composition in an amount from about 0.0001% to about 10% by weight of the composition, more preferably from about 0.0001% to about 5% by weight of the composition, and even more preferably from about 0.0001% to about 1% by weight of the composition.

The laundry care compositions, including laundry detergents, may be in solid or liquid form, including a gel form. The laundry detergent composition comprises a surfactant in an amount sufficient to provide desired cleaning properties. The laundry detergent composition comprises a surfactant in an amount sufficient to provide desired cleaning properties.

In one embodiment, the laundry detergent composition comprises, by weight, from about 5% to about 90% of the surfactant, and more specifically from about 5% to about 70% of the surfactant, and even more specifically from about 5% to about 40%. The surfactant may comprise anionic, nonionic, cationic, zwitterionic and/or amphoteric surfactants. In a more specific embodiment, the detergent composition comprises anionic surfactant, nonionic surfactant, or mixtures thereof.

The detergent compositions of the present invention may also include any number of additional optional ingredients. These include conventional laundry detergent composition components such as non-tinting dyes, detersive builders, enzymes, enzyme stabilizers (such as propylene glycol, boric acid and/or borax), suds suppressors, soil suspending agents, soil release agents, other fabric care benefit agents, pH adjusting agents, chelating agents, smectite clays, solvents, hydrotropes and phase stabilizers, structuring agents, dye transfer inhibiting agents, opacifying agents, optical brighteners, perfumes and coloring agents. The various optional detergent composition ingredients, if present in the compositions herein, should be utilized at concentrations conventionally employed to bring about their desired contribution to the composition or the laundering operation. Frequently, the total amount of such optional detergent composition ingredients can range from about 0.01% to about 50%, more preferably from about 0.1% to about 30%, by weight of the composition.

The whitening agent may be added to textile substrates using a variety of application techniques. For application to textile substrates, the whitening agent is preferably included as an additive in laundry detergent. Thus, application to the textile substrate actually occurs when a consumer adds laundry detergent to a washing machine. Similarly, rinse added fabric softener compositions are typically added in the rinse cycle, which is after the detergent solution has been used and replaced with the rinsing solution in typical laundering processes. For application to paper substrates, the whitening agent may be added to the paper pulp mixture prior to formation of the final paper product.

As noted previously, the detergent compositions may be in a solid form. Suitable solid forms include tablets and particulate forms, for example, granular particles or flakes. Various techniques for forming detergent compositions in such solid forms are well known in the art and may be used herein. In one embodiment, for example when the composition is in the form of a granular particle, the whitening agent is provided in particulate form, optionally including additional but not all components of the laundry detergent composition. The whitening agent particulate is combined with one or more additional particulates containing a balance of components of the laundry detergent composition. Further, the whitening agent, optionally including additional but not all components of the laundry detergent composition, may be provided in an encapsulated form, and the whitening agent encapsulate is combined with particulates containing a substantial balance of components of the laundry detergent composition.

The colorant compositions of this invention, prepared as hereinbefore described, can be used to form laundry care compositions and other household cleaning compositions, including without limitation, aqueous washing solutions for use in the laundering of fabrics, solid surface cleaners, dish and skin cleaners, and shampoos. As one example, an effective amount of a laundry care composition containing the inventive colorant may be added to water, preferably in a conventional fabric laundering automatic washing machine, to form an aqueous laundering solution. The aqueous washing solution so formed is then contacted, preferably under agitation, with the fabrics to be laundered therewith.

Additionally, it is noted that the leuco colorants may be modified as necessary in order to provide stability of the colorant when added as an ingredient to other chemical compositions. For example, certain groups attached to the chromophore of the colorant composition may be modified to provide equilibrium and stability of the colorant in the desired end-use application. For instance, the ionic strength of the end-use application, such as a chemical composition, may affect the equilibrium of the colorant. Accordingly, modifications to the colorant may be made to polymer chains and other groups attached to the colorant, in order to stabilize the colorant and prevent the colorless version of the leuco colorant from changing to the colored version too quickly. As one example, modifications to the colorant may be needed in order to stabilize the colorless state of the colorant when added to certain surfactant-containing compositions, such as laundry detergents and the like. In surfactant-containing compositions, it may be desirable to modify the colorant so that it has the same or very similar surface energy and/or HLB properties as the surfactant-containing composition.

EXAMPLES

The following examples are provided to further illustrate the unsubstituted and polymeric leuco colorants of the present invention; however, they are not to be construed as limiting the invention as defined in the claims appended hereto. In fact, it will be apparent to those skilled in the art that various modifications and variations can be made in this invention without departing from the scope or spirit of the invention. All parts and percents given in these examples are by weight unless otherwise indicated.

Sample Preparation

General Procedure 1: For Nitrile Addition to TPM

The following general procedure was used, for example, to make Colorants 1-12 and 26 from Tables 1 and 2.

A 4-necked 500 mL round bottom flask was equipped with a thermocouple, heating mantle, mechanical stirrer, an air inlet and an outlet connected to an air scrubber bath containing a 10% solution of NaOH. The polymeric triphenylmethane (0.080 mol) was poured into the flask, followed by the addition of sodium cyanide (2M solution, 0.080 mol). The air inlet was turned on, making sure that the outlet was bubbling into the sodium hydroxide bath solution. The mixture was heated to 70° C. for 3 hours, the temperature was then lowered to 25° C. and the alkaline solution was taken to pH 6 using muriatic acid. Further purification may be accomplished by adding activated carbon, heating the mixture to 50° C. and filtering off the activated carbon.

General Procedure 2: For Alkoxide TPM Addition

The following general procedure was used, for example, to make Colorants 13-16, 23, 25, 27 and 28 from Tables 1 and 2.

To a solution of the TPM (0.01 mol) in the corresponding alcohol (6 mL) was added the sodium alkoxide (0.015 mol). The mixture was heated to reflux for 1 hour and then cooled. Removal of the excess alcohol was done via evaporation on a rotary-evaporator or via distillation.

Phenoxides were done in isopropyl alcohol and the excess phenols were left in the mixture.

General Procedure 3: For Amine TPM Addition

The following general procedure was used, for example, to make Colorants 17-20 from Tables 1 and 2.

To a solution of the TPM (0.010 mol) in water (10 mL) was added 10% sodium hydroxide to a pH of 10. The mixture was heated at 70° C. for 2 hours. The pH of the solution was then taken to 7 with muriatic acid. The mixture was then diluted with toluene followed by the addition of the corresponding amine (0.020 mol) and 5-6 drops of acetic acid. The mixture was heated to reflux and the water removed via dean stark distillation. The toluene was evaporated from the mixture to obtain the desired product.

General Procedure 4: For Lactone TPM

The following general procedure was used, for example, to make Colorant 21 from Tables 1 and 2.

4-(4-Dialkylaminobenzoyl)-dialkylamino-3-benzoic acid (0.060 mol) and the aniline alkoxylated (0.061 mol) were mixed together in acetic anhydride for 24 hours at room temperature. After the reaction was completed the pH was taken to 10 with 10% sodium hydroxide and the organic phase was separated and used without further purification. Further purification can be accomplished by extraction of the desired product into methylene chloride followed by removal of the solvent via evaporation. Smaller sized alkoylates may be recrystalized from butanol.

General Procedure 5: For Fluoran Synthesis

The following general procedure was used, for example, to make Colorant 24 from Tables 1 and 2.

2-(4-Dialkylamino-2-hydroxybenzoyl)-benzoic acid (0.01 mol) and p-anisidine alkoxylate (0.015 mol) were dissolved in 10 mL of concentrated sulfuric acid at 40° C. and thereafter stirred at room temperature for 48 hours. After completion of the reaction, the mixture was poured into a mixture of 50 g ice and 50 mL of water. The mixture was taken to pH 10 and the aqueous layer was removed.

Test Results

Calculation of Whiteness: CIELab b* and Ganz and CIE Whiteness Index

Whiteness Index ("WI") is a qualifying assessment of color that is calculated by a formula which includes three components of color measurement—hue, saturation, and lightness—which is then indexed to a standard white value. Several whiteness formulas can be used to measure whiteness on cellulose based substrates. Two common formulas are the Ganz Whiteness Index and CIE Whiteness. Ganz Whiteness Index is expressed by the formula: $WI=(D*Y)+(P*x)+(Q*y)+C$, where Y, x and y are calorimetric values and D, P, Q and C are formula parameters. CIE Whiteness is expressed by the formula: $WI=Y-(800*x)-(1700*y)+813.7$, where Y, x and y are calorimetric values. Higher positive Ganz WI values indicate that more blueing, or whitening effect, is exhibited by the treated cellulose based substrate. Further information is available in the publication of Rolf Griesser, Ciba-Geigy Ltd, "Whiteness and Tint", June 1993.

The surface color of an article may be quantified using a series of measurements—L*, a*, and b*—generated by measuring the samples using a spectrophotometer. The equipment used for this test was a Gretag Macbeth Color Eye 7000A spectrophotometer. The software program used was "Color imatch." "L" is a measure of the amount of white or black in a sample; higher "L" values indicate a lighter colored sample. A measure of the amount of red or green in a sample is determined by "a*" values. A measure of the amount of blue or yellow in a sample is determined by "b*" values; lower (more negative) b* values indicate more blue on a sample.

Yet another measurement of the relative color of a substrate is DE CMC. DE CMC is a measure of the overall color difference for all uniform color spaces, where DE CMC represents the magnitude of difference between a color and a reference. The Gretag Macbeth Color Eye 7000A Spectrophotometer calculates DE CMC values based on wavelength and reflectance data for each sample.

Several polymeric leuco colorants from Tables 1 and 2 were tested for bluing efficiency. Test results are provided in Table 3. Lower (more negative) CIELab b* values indicate that more bluing, or whitening effect, is exhibited by the treated cotton swatch.

Each sample was prepared by adding 0.5 grams of the colorant (0.1% based on weight of the cotton swatch) to a solution containing 3 grams of powdered laundry detergent (AATCC powder laundry detergent) and 500 mL of room temperature water. Each colorant loading was corrected for absorbance to assure equal amount of color units. The formulation was then added to a 100% cotton swatch and agitated for 10 minutes. The swatch was removed from the liquid, the excess liquid was removed, and the swatch was air dried. The cotton swatch was then measured for color using a Gretag Macbeth Color Eye 7000A spectrophotometer, as described previously ("CIELab b* value before UV" and "DE CMC value before UV").

The cotton swatch was then subjected to UV light exposure for 5 minutes. After exposure the cotton swatch was again read on the Gretag Macbeth spectrophotometer ("CIELab b* value after UV" and "DE CMC value after UV").

TABLE 3

Rate of Bluing Efficiency in Detergent on 100% cotton textile

| Sample | CIELab b* Color Value before UV | CIELab b* Color Value after UV | DE CMC Value before UV | DE CMC Value after UV |
|---|---|---|---|---|
| Colorant 9 | 0.59 | −3.12 | 1.32 | 6.05 |
| Colorant 11 | 1.03 | −7.03 | 2.42 | 11.91 |
| Colorant 12 | 1.22 | −2.37 | 0.56 | 5.01 |

Thus, the polymeric leuco colorant of the present invention may be selected from the group consisting of Structure I and Structure II as shown below:

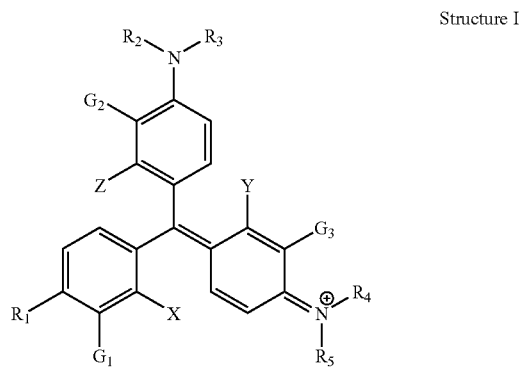

Structure I

-continued

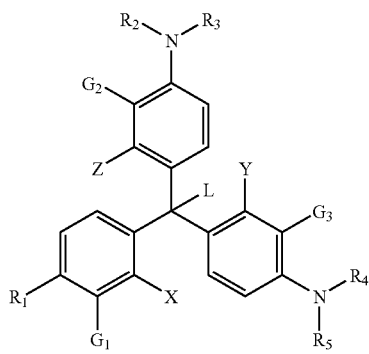

Structure II wherein:

$R_1$=H, dialkyl amine, diarylamine, alkylamine, hydroxyl, halogen, O-alkyl, or polyalkylene oxide amine;

$R_2$=$C_1$-$C_8$ alkyl, aryl, benzyl, polyalkylene oxide, or glycidylether-polyalkylene oxide wherein the terminal group is selected from hydroxide, $C_1$-$C_{18}$ alkyl ester, and an amino substituted with H, $C_1$-$C_{18}$ alkyl, alkyleneoxide residue, or ammonium quaternary salts derived from alkylation of the amino substituted structure;

$R_3$=$C_1$-$C_8$ alkyl, aryl, benzyl, polyalkylene oxide, or glycidylether-polyalkylene oxide wherein the terminal group is selected from hydroxide, $C_1$-$C_{18}$ alkyl ester, and an amino substituted with H, $C_1$-$C_{18}$ alkyl, alkyleneoxide residue, or ammonium quaternary salts derived from alkylation of the amino substituted structure;

$R_4$=$C_1$-$C_8$ alkyl, aryl, benzyl, polyalkylene oxide, or glycidylether-polyalkylene oxide wherein the terminal group is selected from hydroxide, $C_1$-$C_{18}$ alkyl ester, and an amino substituted with H, $C_1$-$C_{18}$ alkyl, alkyleneoxide residue, or ammonium quaternary salts derived from alkylation of the amino substituted structure;

$R_5$=$C_1$-$C_8$ alkyl, aryl, benzyl, polyalkylene oxide, or glycidylether-polyalkylene oxide wherein the terminal group is selected from hydroxide, $C_1$-$C_{18}$ alkyl ester, and an amino substituted with H, $C_1$-$C_{18}$ alkyl, alkyleneoxide residue, or ammonium quaternary salts derived from alkylation of the amino substituted structure;

wherein X=alkyl, H, sulfonate, or carboxylate; $G_{1-3}$, Y, and Z are independently selected from the group of alkyl, H, halogen, nitro, and O-alkyl;

wherein L=$C_1$-$C_{16}$ alkoxide, phenoxide, bisphenoxide, nitrite, nitrile, alkyl amine, imidazole, arylamine, polyalkylene oxide, alkylsulfide, aryl sulfide, or phosphine oxide;

wherein X and $G_1$ taken together may form an aromatic or heteroaromatic ring;

wherein Y and $G_3$ taken together may form an aromatic or heteroaromatic ring;

wherein Z and $G_2$ taken together may form an aromatic or heteroaromatic ring;

wherein $R_2$ and $G_2$ taken together may form an aromatic or heteroaromatic ring;

wherein $R_4$ and $G_3$ taken together may form an aromatic or heteroaromatic ring.

Additionally, the polymeric leuco colorant of the present invention may be selected from the group consisting of Structure I and Structure II as shown below:

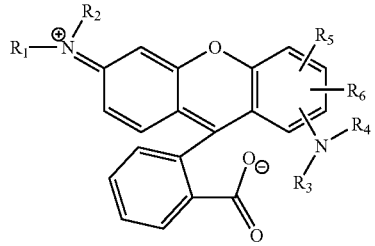

Structure I

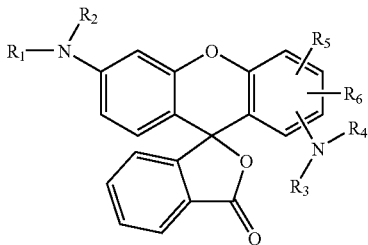

Structure II wherein:

$R_1$=H, alkyl, aryl, or alkyl-aryl wherein the terminal group is selected from hydroxide, $C_1$-$C_{18}$ alkyl ester, and an amino substituted with H, $C_1$-$C_{18}$ alkyl, alkyleneoxide residue, or ammonium quaternary salts derived from alkylation of the amino substituted structure;

$R_2$=H, alkyl, aryl, or alkyl-aryl wherein the terminal group is selected from hydroxide, $C_1$-$C_{18}$ alkyl ester, and an amino substituted with H, $C_1$-$C_{18}$ alkyl, alkyleneoxide residue, or ammonium quaternary salts derived from alkylation of the amino substituted structure;

$R_3$=H, polyalkylene oxide, or glycidylether-polyalkylene oxide wherein the terminal group is selected from hydroxide, $C_1$-$C_{18}$ alkyl ester, and an amino substituted with H, $C_1$-$C_{18}$ alkyl, alkyleneoxide residue, or ammonium quaternary salts derived from alkylation of the amino substituted structure;

$R_4$=$C_1$-$C_{18}$ alkyl, aryl, benzyl, polyalkylene oxide, or glycidylether-polyalkylene oxide wherein the terminal group is selected from hydroxide, $C_1$-$C_{18}$ alkyl ester, and an amino substituted with H, $C_1$-$C_{18}$ alkyl, alkyleneoxide residue, or ammonium quaternary salts derived from alkylation of the amino substituted structure; and $R_5$=H, alkyl, or halogen; and $R_6$=H, alkyl, or halogen.

Also, the polymeric leuco colorant of the present invention may be selected from the group consisting of Structure I and Structure II as shown below:

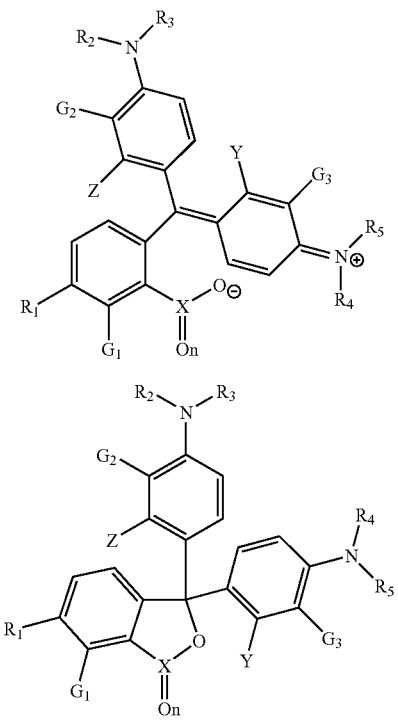

Structure I

Structure II wherein:
R$_1$=H, dialkyl amine, diarylamine, alkylamine, hydroxyl, halogen, O-alkyl, polyalkylene oxide amine, or monoalkyl-polyalkyene oxide amine;
R$_2$=C$_1$-C$_{18}$ alkyl, aryl, benzyl, polyalkylene oxide, or glycidylether-polyalkylene oxide wherein the terminal group is selected from hydroxide, C$_1$-C$_{18}$ alkyl ester, and an amino substituted with H, C$_1$-C$_{18}$ alkyl, alkyleneoxide residue, or ammonium quaternary salts derived from alkylation of the amino substituted structure;
R$_3$=C$_1$-C$_{18}$ alkyl, aryl, benzyl, polyalkylene oxide, or glycidylether-polyalkylene oxide wherein the terminal group is selected from hydroxide, C$_1$-C$_{18}$ alkyl ester, and an amino substituted with H, C$_1$-C$_{18}$ alkyl, alkyleneoxide residue, or ammonium quaternary salts derived from alkylation of the amino substituted structure;
R$_4$=C$_1$-C$_{18}$ alkyl, aryl, benzyl, polyalkylene oxide, or glycidylether-polyalkylene oxide wherein the terminal group is selected from hydroxide, C$_1$-C$_{18}$ alkyl ester, and an amino substituted with H, C$_1$-C$_{18}$ alkyl, alkyleneoxide residue, or ammonium quaternary salts derived from alkylation of the amino substituted structure;
R$_5$=C$_1$-C$_{18}$ alkyl, aryl, benzyl, polyalkylene oxide, or glycidylether-polyalkylene oxide wherein the terminal group is selected from hydroxide, C$_1$-C$_{18}$ alkyl ester, and an amino substituted with H, C$_1$-C$_{18}$ alkyl, alkyleneoxide residue, or ammonium quaternary salts derived from alkylation of the amino substituted structure;
wherein X$_n$=carbon or sulfur and n=1 when X=carbon and n=2 when X=sulfur;
G$_{1-3}$, Y, and Z are independently selected from the group of alkyl, H, halogen, nitro, and O-alkyl;
wherein Y and G$_3$ taken together may form an aromatic or heteroaromatic ring;
wherein Z and G$_2$ taken together may form an aromatic or heteroaromatic ring;
wherein R$_2$ and G$_2$ taken together may form an aromatic or heteroaromatic ring;
wherein R$_4$ and G$_3$ taken together may form an aromatic or heteroaromatic ring.

The invention described herein encompasses a method for imparting color to a composition comprises the steps of: (a) adding a sufficient amount of any of the Structure II polymeric colorants as described and shown herein to a composition; (b) exposing the composition of step "a" to a physical or chemical change that causes Structure II to change to the corresponding Structure I; nd (c) optionally, eliminating the imparted color from the composition by removing the physical or chemical change from the composition and causing Structure I to change back to Structure II.

The invention described herein also encompasses a method for imparting hue to a surface comprising the steps of: (a) adding a sufficient amount of any of the Structure II polymeric colorants as described and shown herein to a cleaning composition; (b) exposing a surface to the cleaning composition of step "a;" and (c) imparting a physical or chemical change to the composition of step "b" that causes Structure II to change to the corresponding Structure I.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:
1. A polymeric leuco colorant selected from the group consisting of Structure I and Structure II as shown below:

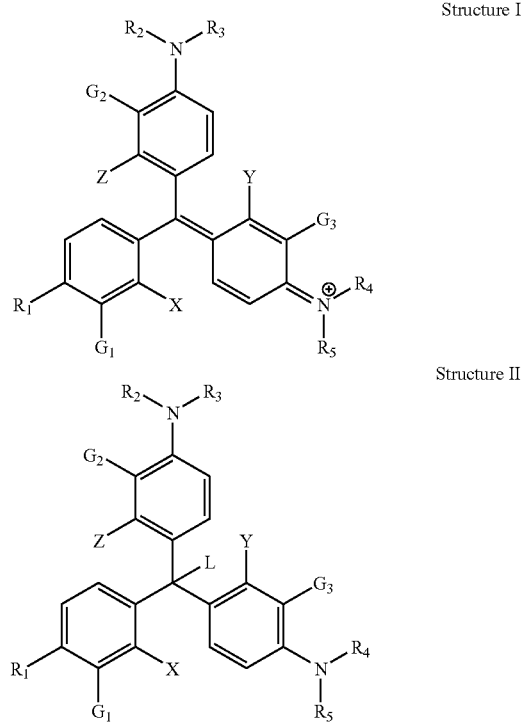

Structure I

Structure II wherein:
R$_1$=H, dialkyl amine, diarylamine, alkylamine, hydroxyl, halogen, O-alkyl, or polyalkylene oxide amine;

$R_2=C_1-C_8$ alkyl, aryl, benzyl, polyalkylene oxide, or glycidylether-polyalkylene oxide wherein the terminal group is selected from hydroxide, $C_1-C_{18}$ alkyl ester, and an amino substituted with H, $C_1-C_{18}$ alkyl, alkyleneoxide residue, or ammonium quaternary salts derived from alkylation of the amino substituted structure;

$R_3=C_1-C_8$ alkyl, aryl, benzyl, polyalkylene oxide, or glycidylether-polyalkylene oxide wherein the terminal group is selected from hydroxide, $C_1-C_{18}$ alkyl ester, and an amino substituted with H, $C_1-C_{18}$ alkyl, alkyleneoxide residue, or ammonium quaternary salts derived from alkylation of the amino substituted structure;

$R_4=C_1-C_8$ alkyl, aryl, benzyl, polyalkylene oxide, or glycidylether-polyalkylene oxide wherein the terminal group is selected from hydroxide, $C_1-C_{18}$ alkyl ester, and an amino substituted with H, $C_1-C_{18}$ alkyl, alkyleneoxide residue, or ammonium quaternary salts derived from alkylation of the amino substituted structure;

$R_5=C_1-C_8$ alkyl, aryl, benzyl, polyalkylene oxide, or glycidylether-polyalkylene oxide wherein the terminal group is selected from hydroxide, $C_1-C_{18}$ alkyl ester, and an amino substituted with H, $C_1-C_{18}$ alkyl, alkyleneoxide residue, or ammonium quaternary salts derived from alkylation of the amino substituted structure;

wherein X=alkyl, H, sulfonate, or carboxylate; $G_{1-3}$, Y, and Z are independently selected from the group of alkyl, H, halogen, nitro, and O-alkyl;

wherein L=$C_1-C_{16}$ alkoxide, phenoxide, bisphenoxide, nitrite, nitrile, alkyl amine, imidazole, arylamine, polyalkylene oxide, alkylsulfide, aryl sulfide, or phosphine oxide;

wherein X and $G_1$ taken together may form an aromatic or heteroaromatic ring;

wherein Y and $G_3$ taken together may form an aromatic or heteroaromatic ring;

wherein Z and $G_2$ taken together may form an aromatic or heteroaromatic ring;

wherein $R_2$ and $G_2$ taken together may form an aromatic or heteroaromatic ring;

wherein $R_4$ and $G_3$ taken together may form an aromatic or heteroaromatic ring.

2. The polymeric colorant of claim 1, wherein $R_1$=dialkyl amine; X=H; Y=H; Z=H or alkyl; $G_{1-3}$=H;; and L=nitrile.

3. The polymeric colorant of claim 2, wherein $R_2$ and $R_5$ are the same and wherein $R_3$ and $R_4$ are the same.

4. The polymeric colorant of claim 2, wherein Z=alkyl; $R_2=C_1-C_8$ alkyl and $R_5=C_1-C_8$ alkyl and wherein $R_3$=polyalkylene oxide and $R_4$=polyalkylene oxide.

5. The polymeric colorant of claim 2, wherein Z=H; $R_2$=aryl and $R_5$=aryl and wherein $R_3$=polyalkylene oxide and $R_4$=polyalkylene oxide.

6. The polymeric colorant of claim 2, wherein Z=alkyl; $R_2$=glycidylether-polyalkylene oxide and $R_5$=glycidylether-polyalkylene oxide and wherein $R_3$=glycidylether-polyalkylene oxide and $R_4$=glycidylether-polyalkylene oxide.

7. The polymeric colorant of claim 2, wherein Z=alkyl; $R_2$=aryl and $R_5$=aryl and wherein $R_3$=polyalkylene oxide and $R_4$=polyalkylene oxide.

8. The polymeric colorant of claim 2, wherein Z=H; $R_2$=polyalkylene oxide and $R_5$=polyalkylene oxide and wherein $R_3$=polyalkylene oxide and $R_4$=polyalkylene oxide.

9. The polymeric colorant of claim 2, wherein $R_2$ and $R_4$ are the same and wherein $R_3$ and $R_5$ are the same.

10. The polymeric colorant of claim 9, wherein Z=H; $R_2$=glycidylether-polyalkylene oxide and $R_4$=glycidylether-polyalkylene oxide and wherein $R_3$=glycidylether-polyalkylene oxide and $R_5$=glycidylether-polyalkylene oxide.

11. The polymeric colorant of claim 9, wherein Z=alkyl; $R_2$=glycidylether-polyalkylene oxide and $R_4$=glycidylether-polyalkylene oxide and wherein $R_3$=glycidylether-polyalkylene oxide and $R_5$=glycidylether-polyalkylene oxide.

12. The polymeric colorant of claim 9, wherein Z=alkyl; $R_2$=aryl and $R_4$=aryl and wherein $R_3$=glycidylether-polyalkylene oxide and $R_5$=glycidylether-polyalkylene oxide.

13. The polymeric colorant of claim 9, wherein Z=H; $R_2$=aryl and $R_4$=aryl and wherein $R_3$=glycidylether-polyalkylene oxide and $R_5$=glycidylether-polyalkylene oxide.

14. The polymeric colorant of claim 9, wherein Z=H; and wherein $R_2$=aryl and $R_4$=aryl and wherein $R_3$=polyalkylene oxide and $R_5$=polyalkylene oxide.

15. The polymeric colorant of claim 2, wherein $R_2$, $R_3$, $R_4$ and $R_5$ are the same.

16. The polymeric colorant of claim 15, wherein Z=H and wherein $R_2$, $R_3$, $R_4$ and $R_5$ are polyalkylene oxide having terminal hydroxide groups.

17. The polymeric colorant of claim 1, wherein $R_1$=dialkyl amine or H; X=H or sulfonate; Y=H; Z=H; $G_{1-3}$=H; wherein $R_2$ and $R_5$ are the same, and wherein $R_3$ and $R_4$ are the same.

18. The polymeric colorant of claim 17, wherein L=$C_1-C_{16}$ alkoxide.

19. The polymeric colorant of claim 18, wherein $R_2$ and $G_2$ form a cyclic ring.

20. The polymeric colorant of claim 17, wherein L=nitrile.

21. The polymeric colorant of claim 17, wherein L=polyalkylene oxide.

22. The polymeric colorant of claim 1, wherein $R_1$=dialkyl amine; X=H; Y=H; Z=H;
$G_{1-3}$=H; wherein each of $R_2$ and $R_5$ are polyalkylene oxide having the same chain length, and wherein $R_3$ and $R_4$ are polyalkylene oxide having the same chain length.

23. The polymeric colorant of claim 22, wherein L=arylamine.

24. The polymeric colorant of claim 22, wherein L=imidazole.

25. The polymeric colorant of claim 22, wherein L=cycloalkyl amine.

26. A chemical composition comprising the polymeric colorant of claim 1.

27. A detergent composition comprising the polymeric colorant of claim 1.

28. A method for imparting color to a composition comprising the steps of:
    (a) adding a sufficient amount of the Structure II polymeric colorant of claim 1 to a composition;
    (b) exposing the composition of step "a" to a physical or chemical change that causes Structure II to change to Structure I; and
    (c) optionally, eliminating the imparted color from the composition by removing the physical or chemical change from the composition and causing Structure I to change back to Structure II.

29. The method of claim 28, wherein the physical or chemical change of step "b" is selected from one of the following: exposure to oxygen, exposure to heat, exposure to ultraviolet light, the addition of acid, the addition of base, reaction with strong ions, the addition of solvent, the addition of reducing agents and any mixtures thereof.

30. A method for imparting hue to a textile substrate comprising the steps of:
    (a) adding a sufficient amount of the Structure II polymeric colorant of claim 1 to a laundry care composition;
    (b) exposing a textile substrate to the laundry care composition of step "a;" and (c) imparting a physical or chemical change to the composition of step "b" that causes Structure II to change to Structure I.

31. A method for imparting hue to a surface comprising the steps of:
(a) adding a sufficient amount of the Structure II polymeric colorant of claim 1 to a cleaning composition;
(b) exposing a surface to the cleaning composition of step "a;" and
(c) imparting a physical or chemical change to the composition of step "b" that causes Structure II to change to Structure I.

* * * * *